United States Patent
Ho et al.

(10) Patent No.: US 12,015,197 B2
(45) Date of Patent: Jun. 18, 2024

(54) RADIO-WAVE CONFINEMENT ON METAMATERIAL TEXTILES FOR WIRELESS SENSOR NETWORKING

(71) Applicant: NATIONAL UNIVERSITY OF SINGAPORE, Singapore (SG)

(72) Inventors: John Ho, Singapore (SG); Chee Keong Tee, Singapore (SG); Xi Tian, Singapore (SG); Pui Mun Lee, Singapore (SG)

(73) Assignee: NATIONAL UNIVERSITY OF SINGAPORE, Singapore (SG)

(*) Notice: Subject to any disclaimer, the term of this patent is extended or adjusted under 35 U.S.C. 154(b) by 510 days.

(21) Appl. No.: 17/286,496

(22) PCT Filed: Oct. 17, 2019

(86) PCT No.: PCT/SG2019/050515
§ 371 (c)(1),
(2) Date: Apr. 19, 2021

(87) PCT Pub. No.: WO2020/081010
PCT Pub. Date: Apr. 23, 2020

(65) Prior Publication Data
US 2021/0344109 A1    Nov. 4, 2021

(30) Foreign Application Priority Data
Oct. 19, 2018  (SG) .......................... 10201809262T

(51) Int. Cl.
*H01Q 1/00* (2006.01)
*A41D 1/00* (2018.01)
(Continued)

(52) U.S. Cl.
CPC ............. *H01Q 1/364* (2013.01); *A41D 1/002* (2013.01); *A61B 5/0024* (2013.01); *H01Q 7/00* (2013.01); *H04W 84/18* (2013.01)

(58) Field of Classification Search
CPC .......... H01Q 1/364; H01Q 7/00; H01Q 1/085; H01Q 1/273; H01Q 1/38; H01Q 13/26;
(Continued)

(56) References Cited

U.S. PATENT DOCUMENTS 9,482,784 B2 * 11/2016  Yen ..................... G01N 21/553
9,594,262 B2 *  3/2017  Zheludev ............... G02B 1/002
(Continued)

FOREIGN PATENT DOCUMENTS

CN      103882730 A      6/2014
CN      108493597 A      9/2018

OTHER PUBLICATIONS

Mona Nafari et al., Metallic Plasmonic Nano-antenna for Wireless Optical Communication in Intra-body Nanonetworks. Proceedings of the 10th EAI International Conference on Body Area Networks, Sep. 30, 2015, pp. 287-293.

(Continued)

*Primary Examiner* — Jean B Jeanglaude
(74) *Attorney, Agent, or Firm* — SOROKER AGMON NORDMAN PTE LTD

(57) ABSTRACT

There is provided a metamaterial textile for providing wireless sensor network and method of designing such. The metamaterial textile comprising a sheet of metamaterial textile cut into a comb shape comprising long base with a plurality of metamaterial textile teeth extending along and from the base, wherein a gap is present between every two adjacent teeth, whereby, the metamaterial textile is configured to enable propagation of radio-surface plasmons wave along the metamaterial textile for providing wireless sensor (Continued)

network. The metamaterial textile is configured to control the height of the radio-surface plasmons wave by changing number of the metamaterial textile teeth, and changing dimensions of the metamaterial textile teeth and changing dimensions of the gaps.

17 Claims, 16 Drawing Sheets

(51) Int. Cl.
*A61B 5/00* (2006.01)
*H01Q 1/36* (2006.01)
*H01Q 7/00* (2006.01)
*H04W 84/18* (2009.01)

(58) Field of Classification Search
CPC .... A41D 1/002; A61B 5/0024; A61B 5/6805; H04W 84/18; H04W 88/00; G01S 13/00
USPC ......................................................... 343/904
See application file for complete search history.

(56) References Cited

U.S. PATENT DOCUMENTS

| | | |
|---|---|---|
| 2013/0064311 A1 | 3/2013 | Turner et al. |
| 2014/0131559 A1* | 5/2014 | Yen ...................... G01N 21/553 |
| | | 250/221 |
| 2014/0180624 A1 | 6/2014 | Nikonov et al. |
| 2019/0058242 A1* | 2/2019 | Tabe ...................... H01Q 1/248 |

OTHER PUBLICATIONS

Bahareh Moradi et al., Effect of smart textile metamaterials on electromagnetic performance for wireless body area network systems. Textile Research Journal, Sep. 30, 2018, vol. 89, No. 14, pp. 2892-2899.

Xi Tian et al., Wireless body sensor networks based on metamaterial textiles. Nature Electronics, Jun. 17, 2019, vol. 2, pp. 243-251.

* cited by examiner

FIG. 1B
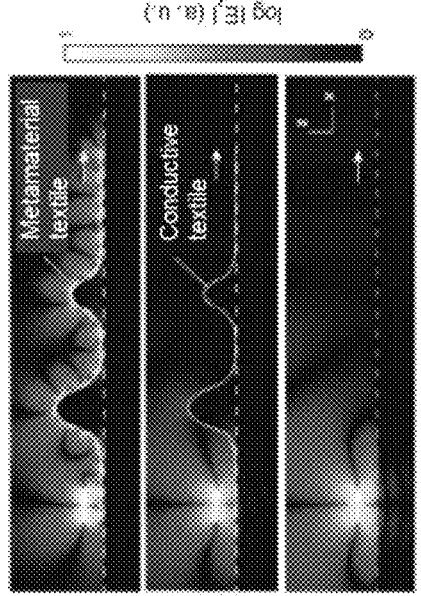
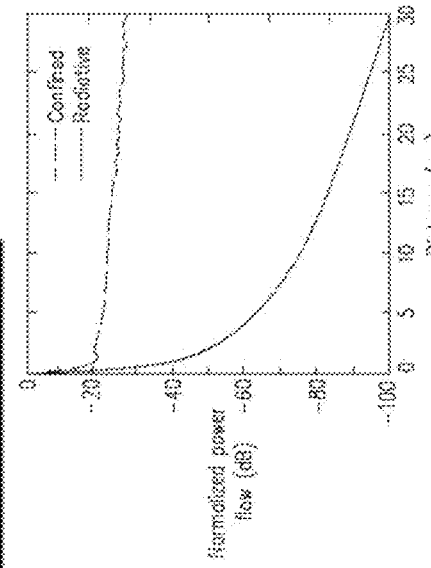
FIG. 1C
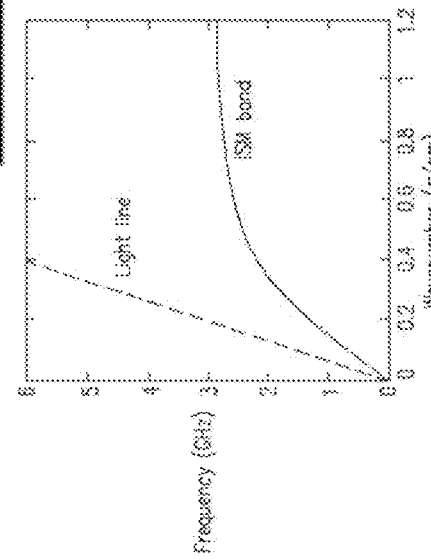
FIG. 1E
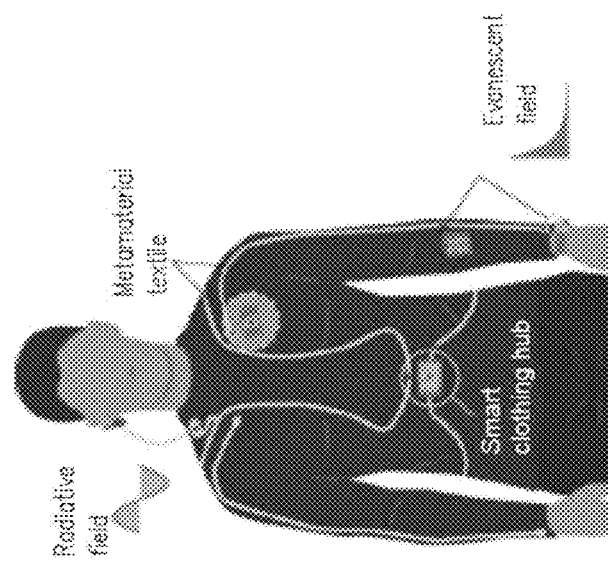
FIG. 1A
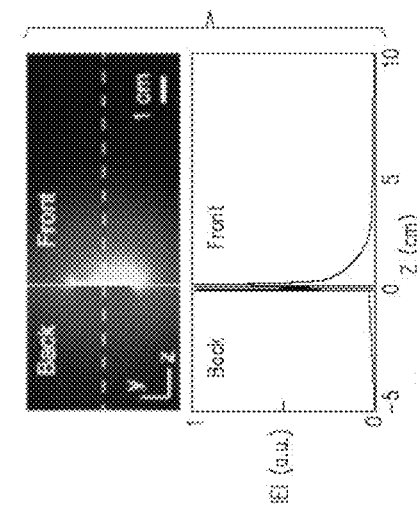
FIG. 1D
FIG. 1F

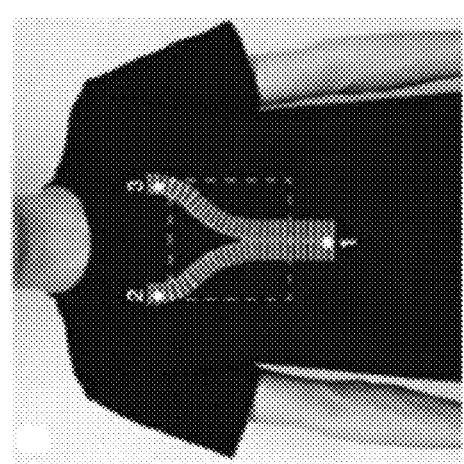
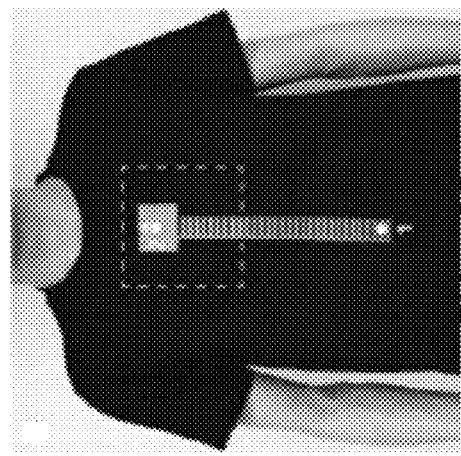
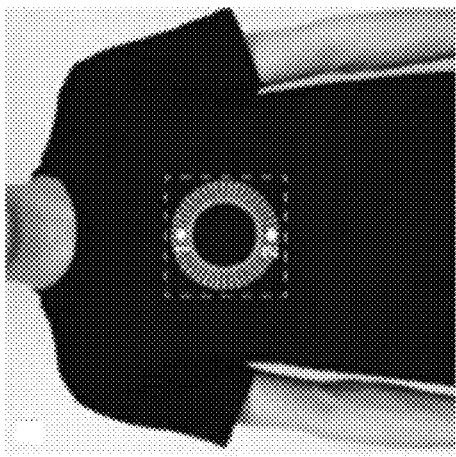
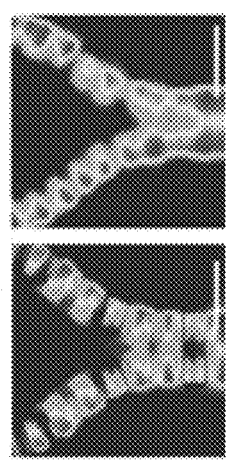
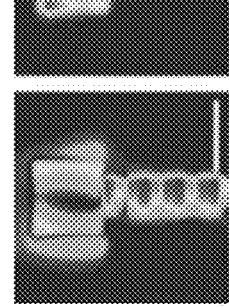
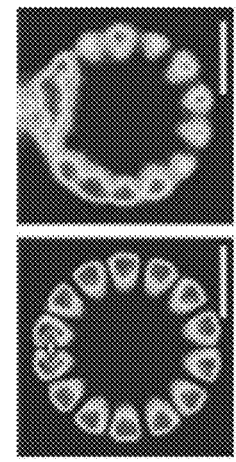
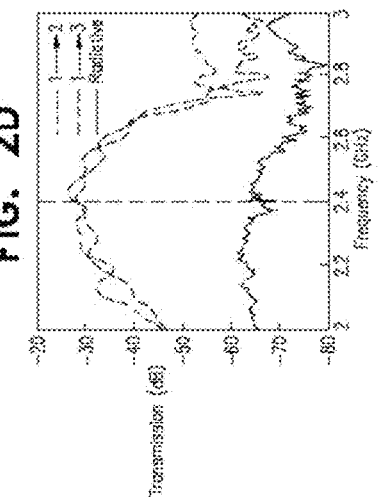
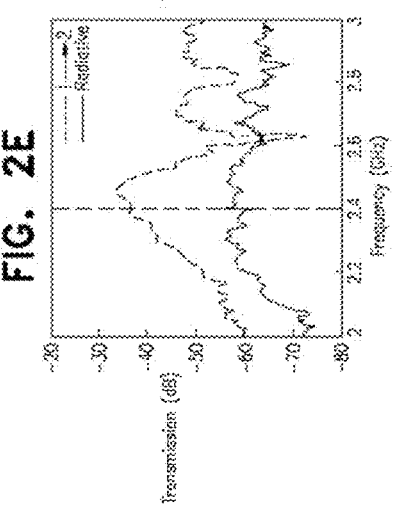
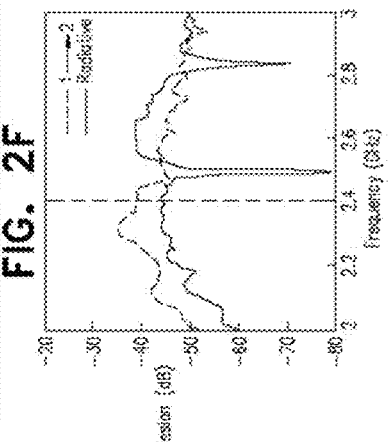
FIG. 2A  FIG. 2B  FIG. 2C
FIG. 2D  FIG. 2E  FIG. 2F
FIG. 2G  FIG. 2H  FIG. 2I

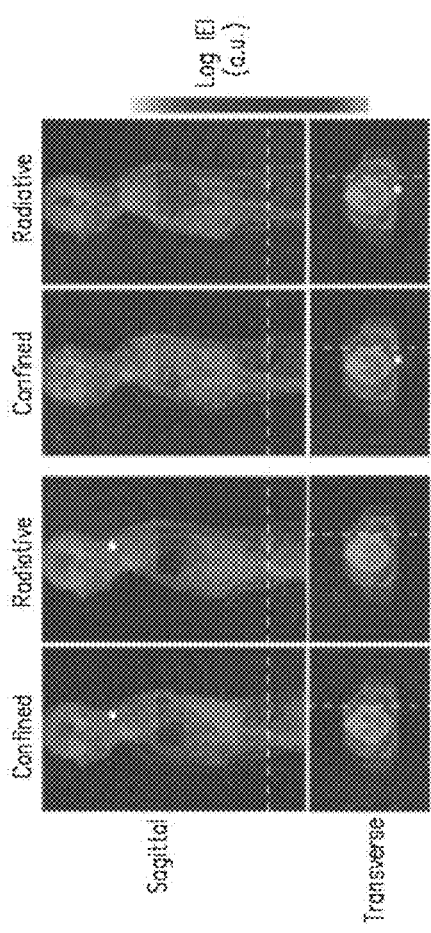
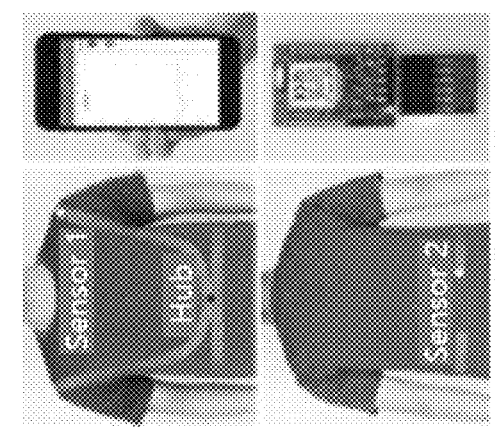
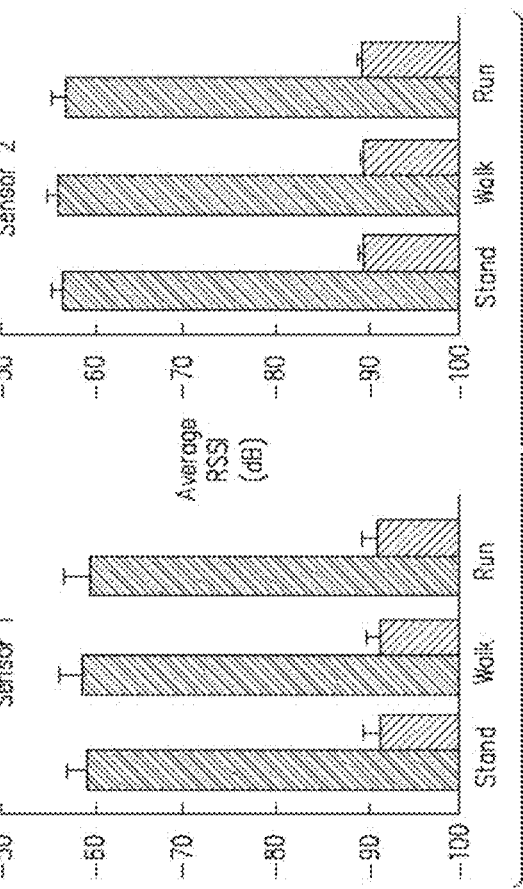
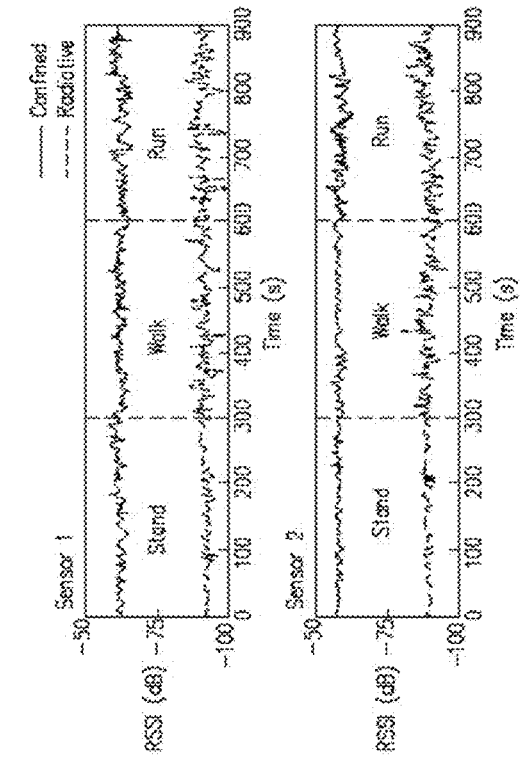
FIG. 3A
FIG. 3B
FIG. 3C
FIG. 3D

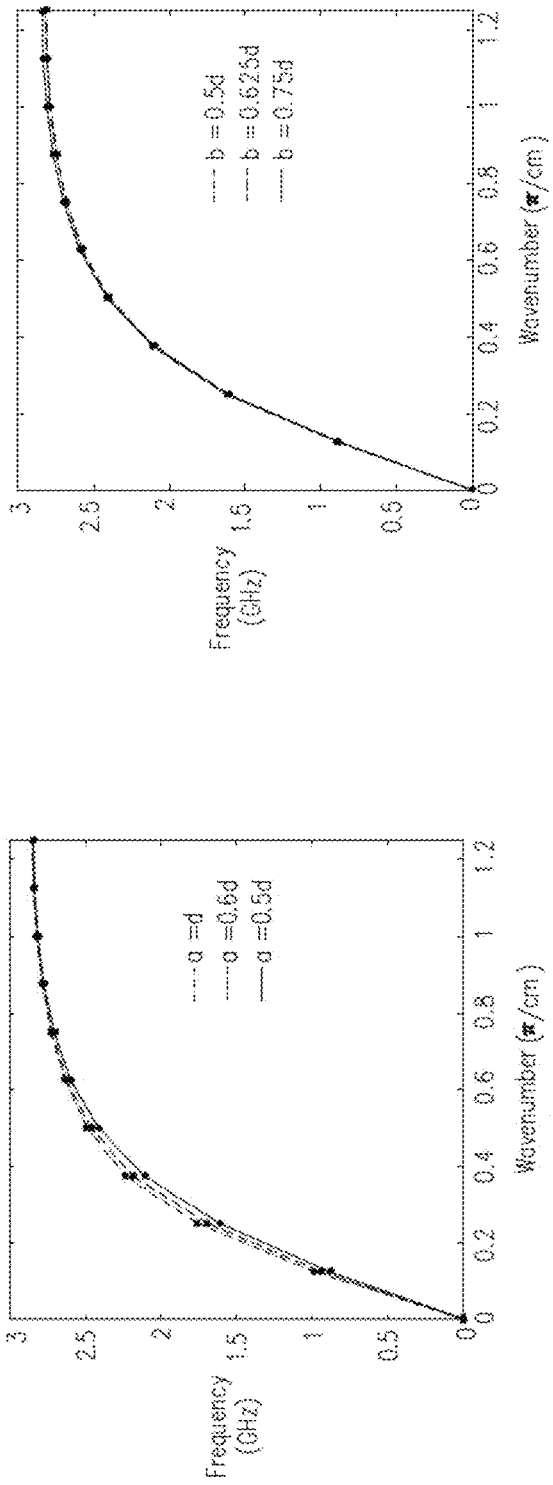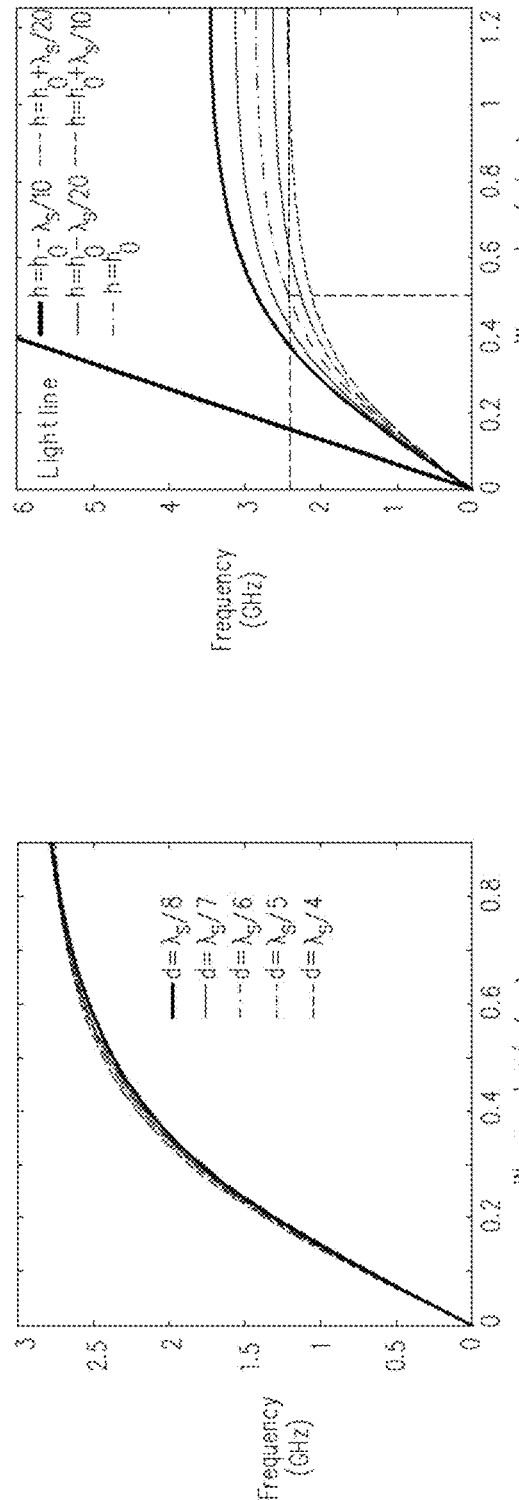
FIG. 5B
FIG. 5C
FIG. 5D
FIG. 5E

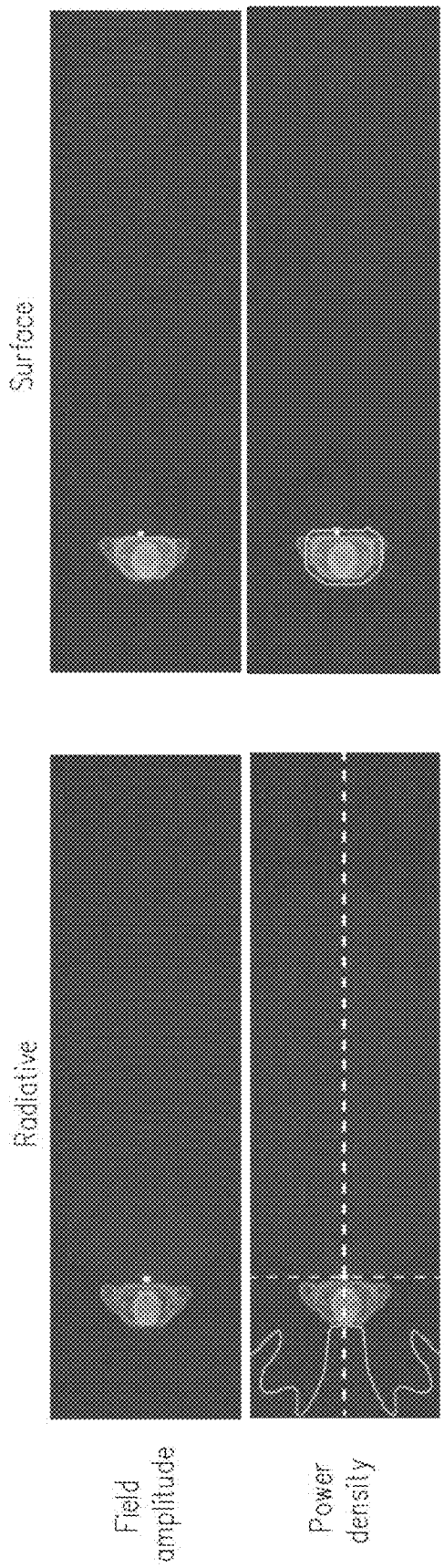
FIG. 11A
FIG. 11B
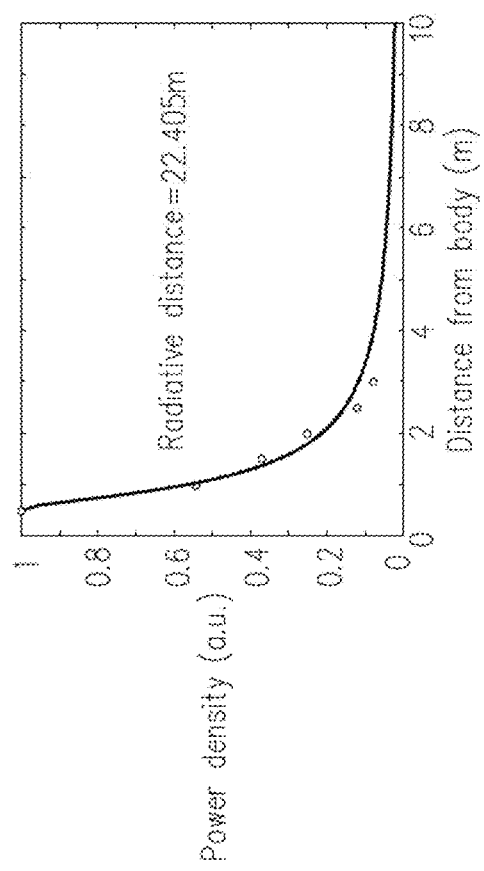
FIG. 11C

RADIO-WAVE CONFINEMENT ON METAMATERIAL TEXTILES FOR WIRELESS SENSOR NETWORKING

TECHNICAL FIELD

The present disclosure generally relates to radio-wave confinement on textile patterns for wireless sensor networking, and more specifically a system and method to confine radio-waves onto clothing patterned with conductive textiles (metamaterial textiles).

BACKGROUND

Over the past decade, rapid progress has been made in the development of sensors, displays, and smart devices that integrate seamlessly with the body. Wireless networks of sensors, displays, and smart devices on the body offer powerful capabilities for health monitoring, human-machine interfaces, and other emerging technological applications.

For instance, direct wiring between sensor nodes is widely used in clinical and research settings, but such approaches disrupt physical activity and are not compatible with continuous use. Recent advances in flexible electronics enable the integration of distributed sensors into clothing or onto skin, but do not address the interconnection of discrete devices.

Meanwhile, wireless networks of wearable devices have so far been limited by challenges in radiative loss, interference, and data security that are inherent to the use of radio-wave radiation into the surrounding space. Despite promising advances in advanced communication circuits and protocols, such wireless networks have not yet been widely adopted owing primarily to energy constraints and limited sensors lifetime.

There is therefore a need for systems and methods that enable efficient and secure transmission of wireless signals between devices worn on or implanted in a user's body, such as sensors, medical implants, headphones, displays, and smart devices, or that enable transfer of power to devices around the body of the user.

SUMMARY

According to embodiments of the disclosure, there is provided an efficient and secure method for confining radio-waves onto clothing patterned with conductive textiles. Wireless signals transmitted near these textile patterns, referred to as "metamaterial textiles", propagate along the surface of the textile rather than into the surrounding space, via plasmonic phenomena. The geometry of the metamaterial textiles may be modified to direct the propagation of radio-waves and to implement passive devices for applications in energy transfer, sensing, and signal processing.

According to embodiments of the present disclosure, the metamaterial textiles of the present disclosure may enable efficient and secure transmission of wireless signals between devices worn on or implanted in the body of a user. Wireless networks of such devices based on the metamaterial textiles may be used to transmit information securely or to transfer power to devices around the body of the user. The metamaterial textiles may also be used as sensing elements by implementing changes in their wireless transmission properties via changes in geometric and environmental variables.

According to some embodiments, these textile patterns, termed metamaterial textiles, may enhance transmission efficiencies by many orders of magnitude and enable wireless transfer of power to sensors on the body of a user. Endowing clothing with such unprecedented electromagnetic capabilities may enable new opportunities for wearable technology.

According to embodiments of the present disclosure, there is provided a metamaterial textile, said metamaterial textile comprising a sheet of metamaterial textile cut into a comb shape comprising long base with a plurality of teeth extending along and from the base, wherein a gap is present between every two adjacent teeth.

The metamaterial textile is configured to enable propagation of radio-surface plasmons wave along the metamaterial textile for providing wireless sensor networks.

The metamaterial textile is configured to control the height of the radio-surface plasmons wave by changing number of the metamaterial textile teeth, and changing dimensions of the metamaterial textile teeth and of changing dimensions of the gaps.

According to some embodiments, there is provided a metamaterial textile for providing wireless sensor network. The metamaterial textile may comprise a sheet of metamaterial textile cut into a comb shape comprising long base with a plurality of metamaterial textile teeth extending along and from the base, whereby a gap is present between every two adjacent teeth. According to some embodiments, the metamaterial textile may be configured to enable propagation of radio-surface plasmons wave along the metamaterial textile for providing wireless sensor network, the radio-surface plasmons wave comprising a height. In some embodiments, the metamaterial textile may be configured to control the height of the radio-surface plasmons wave by changing number of the metamaterial textile teeth, and changing dimensions of the metamaterial textile teeth and changing dimensions the gaps.

Optionally, the maximum number of teeth to enable propagation of radio-surface plasmons along the comb shaped metamaterial textile may be 100.

Optionally, the minimum number of teeth to enable propagation of radio-surface plasmons along the comb shaped metamaterial textile may be two.

Optionally, the comb shaped metamaterial textile may be configured to be implemented as part of clothing.

Optionally, the comb shaped metamaterial textile may comprise a non-conductive layer attached to the comb shaped metamaterial textile.

Optionally, the comb shaped metamaterial textile may further comprise a protective conductive layer attached to and located beneath the non-conductive layer.

Optionally, the non-conductive layer attached to the comb shaped metamaterial textile may block the propagation of radio-surface plasmons into body of a wearer of clothing.

Optionally, the non-conductive layer is textile.

Optionally, the comb shaped metamaterial textile may be configured to form a ring-resonator.

Optionally, the comb shaped metamaterial textile may be configured to form an antenna for transmitting data.

Optionally, the comb shaped metamaterial textile may be configured to form a power divider for transmitting power to more than one location.

Optionally, the radio-surface plasmons wave may have little to no signal loss even at low dB transmission.

According to some embodiments, there is provided a method for designing a metamaterial textile for providing wireless sensor networks. The method may comprise providing a metamaterial textile comprising: a sheet of metamaterial textile cut into a comb shape comprising a long base with a plurality of metamaterial textile teeth extending along and from the base, whereby a gap is present between every two adjacent teeth, providing wireless sensor network via propagation of radio-surface plasmons wave along the comb shaped metamaterial textile; and controlling height of the radio-surface plasmons wave by changing number of the metamaterial textile teeth, and by changing dimensions of the metamaterial textile teeth and dimensions of metamaterial textile gaps.

According to embodiments of the present disclosure, there is provided another method for designing a metamaterial textile for providing wireless sensor networks. The method may comprise providing a metamaterial textile comprising: a sheet of metamaterial textile cut into a comb shape comprising a long base with a plurality of metamaterial textile teeth extending along and from the base, whereby a gap is present between every two adjacent teeth, whereby the comb shaped metamaterial textile may comprise a non-conductive layer attached to the comb shaped metamaterial textile; setting value of width of each of the plurality of metamaterial textile teeth with the addition of width of a gap to: $d=0.2\lambda_s$; setting values of width of each of the plurality of metamaterial textile teeth and of width of the comb shaped base to specific values; setting value of length of each of the plurality of metamaterial textile teeth to $$h_0 = \frac{\pi c}{4\pi\varepsilon_{tex}f_0};$$

setting value of width of the bottom non-conductive layer to: w=a+h; providing thickness of the metamaterial comb shaped textile: implementing varying lengths of each of the plurality of metamaterial textile teeth between $0.5h_0$ and $2h_0$ into an eigenmode solver, thereby obtaining dispersion curve of the metamaterial textile: yielding the value for which $\beta=\beta_s$ wherein $\beta_s$ is desired wavenumber based on the dispersion curve; and calculating $\lambda_s=2\pi/\beta_s$, wherein $\lambda_s$ is surface plasmon wavelength for providing wireless sensor networks.

Optionally, setting value of the width of each of the plurality of metamaterial textile teeth may comprise setting the value to b=0.75. Optionally, setting value of the width of the comb shaped base comprises setting the value to a=0.5d.

Optionally, setting value of width of each of the plurality of metamaterial textile teeth with the addition of width of a gap comprises setting the value according to a different equation than $d=0.2\lambda_s$.

BRIEF DESCRIPTION OF THE DRAWINGS

FIG. 1A is a schematic illustration of a sensor network interconnected by radio-waves confined on clothing, according to embodiments of the present disclosure;

FIG. 1B is a schematic illustration of a structure of the metamaterial textile, according to embodiments of the present disclosure;

FIG. 1C is a schematic illustration of simulation of the electric field distribution |Ez| emitted by a dipole above a metamaterial textile (top figure), unpatterned conductive textile (middle figure), and nonconductive textile (bottom figure), the textile is placed on the body modeled by air-tissue half-space, according to embodiments of the present disclosure:

FIG. 1D is a schematic illustration of normalized field distribution on the 'yz' plane and field profile along the dashed line, according to embodiments of the present disclosure;

FIG. 1E is a schematic illustration of dispersion curve of the metamaterial structure, according to embodiments of the present disclosure;

FIG. 1F is a schematic illustration of comparison of the normalized power flow (peak value of the Poynting vector) with distance from transmitter near the textile (confined) and in free-space (radiative), according to embodiments of the present disclosure;

FIGS. 2A-C are schematic illustrations of devices constructed from the metamaterial textiles: (A) power divider, (B) antenna, and (C) ring-resonator, respectively, according to embodiments of the present disclosure:

FIGS. 2D-F are schematic illustrations of simulation (left) and near-field measurement (right) of the normal component of the electric field above the textile surface during continuous wave excitation at position 1 with a dipole probe, according to embodiments of the present disclosure;

FIGS. 2G-I are schematic illustrations of transmission spectra between antennas placed 5 mm above labeled positions on the body, according to embodiments of the present disclosure;

FIG. 3A is a schematic illustration of wireless network of two Bluetooth nodes (sensors 1 and 2) simultaneously transmitting data to a smartphone (hub), according to embodiments of the present disclosure:

FIG. 3B is a schematic illustration of full-wave simulations of wireless transmission in a computational human body model, according to embodiments of the present disclosure;

FIG. 3C is a schematic illustration of a relative signal strength indicator (RSSI) recorded by the smartphone from each sensor during physiological activity, according to embodiments of the present disclosure;

FIG. 3D is a schematic illustration of a comparison of RSSI averaged across each activity, according to embodiments of the present disclosure;

FIG. 5A(2) is a schematic flow chart depicting a method for manufacturing metamaterial textile, according to embodiments of the present disclosure;

FIGS. 5B-5E are schematic illustrations of dispersion curves as the parameters a, b, d and h, respectively, are varied, according to embodiments of the present disclosure;

FIGS. 11A-11B are schematic illustrations of instantaneous electric field amplitude and time-averaged power density S (logarithmic scale) for a dipole transmitter placed on the front (abdominal region) of a computational human body model without (radiative) and with (surface) the metamaterial textiles in FIG. 7A, according to embodiments of the present disclosure;

FIG. 11C is a schematic illustration of power density radiated in front of the body along the dotted white line in FIG. 11A, according to embodiments of the present disclosure:

Figure 3E:
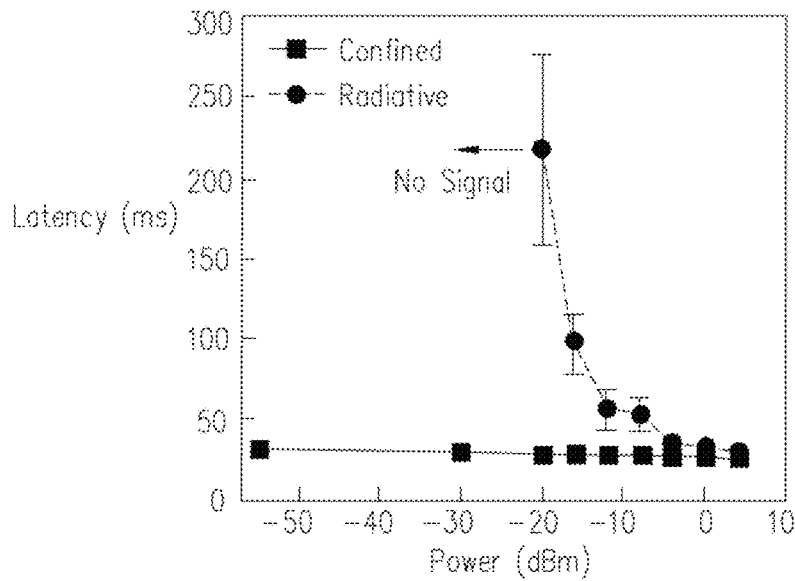
FIG. 3E is a schematic illustration of wireless transmission (Bluetooth) latency as a function of transmit power, according to embodiments of the present disclosure.

The foregoing will be apparent from the following more particular description of example embodiments of the disclosure, as illustrated in the accompanying drawings in which like reference characters refer to the same parts throughout the different views. The drawings are not necessarily to scale: emphasis instead being placed upon illustrating embodiments of the present disclosure.

DETAILED DESCRIPTION

Electromagnetic waves at optical frequencies can be confined on metallic surfaces in localized excitations called surface plasmons. Because these modes propagate conformally along the surface of the metallic material and interact strongly with nearby objects through an evanescent field, they are widely used as interconnection elements in photonic devices. Although surface plasmons do not feature in bulk materials at radio-frequencies, concepts in metamaterials may enable these modes to be engineered by structuring conductive surfaces.

According to embodiments of the present disclosure, clothing structured with conductive textiles may support surface plasmon-like modes at radio communication frequencies and thereby provide a platform to mold the propagation of radio-waves around the body of a user. By physically localizing wireless signals onto the body of a user, such metamaterial textiles may enable personal networks of wireless sensors and devices that are highly efficient, immune to interference, and inherently secure.

Existing metamaterial designs, however, have not been designed for use on the human body, whose complex electromagnetic environment poses challenges in tissue losses and interactions with nearby wireless devices.

According to the present disclosure, these challenges are overcome to enable efficient and secure interconnection of sensor networks with radio surface plasmons. In contrast with conventional wireless communication systems, networks based on presently disclosed metamaterial textiles are interconnected by radio-wave surface plasmons that propagate along structures patterned on clothing. These networks are not subject to inverse square law losses inherent to radiative transmission and require physical proximity to the body of the user in order to transmit and receive signals through interactions mediated by an evanescent field. Because clothing integrated with such metamaterials may be comprised entirely of fabric and may not involve active electronic components, they may be robust to daily wear and may be washed without any harm to the clothing or to its signal transmission capabilities.

According to embodiments of the present disclosure, networks interconnected in this way enhance energy efficiency by many orders of magnitude and meet requirements for wireless power transfer, enabling distribution of power to batteryless sensors on the body of a user.

Figures 2, 5A:
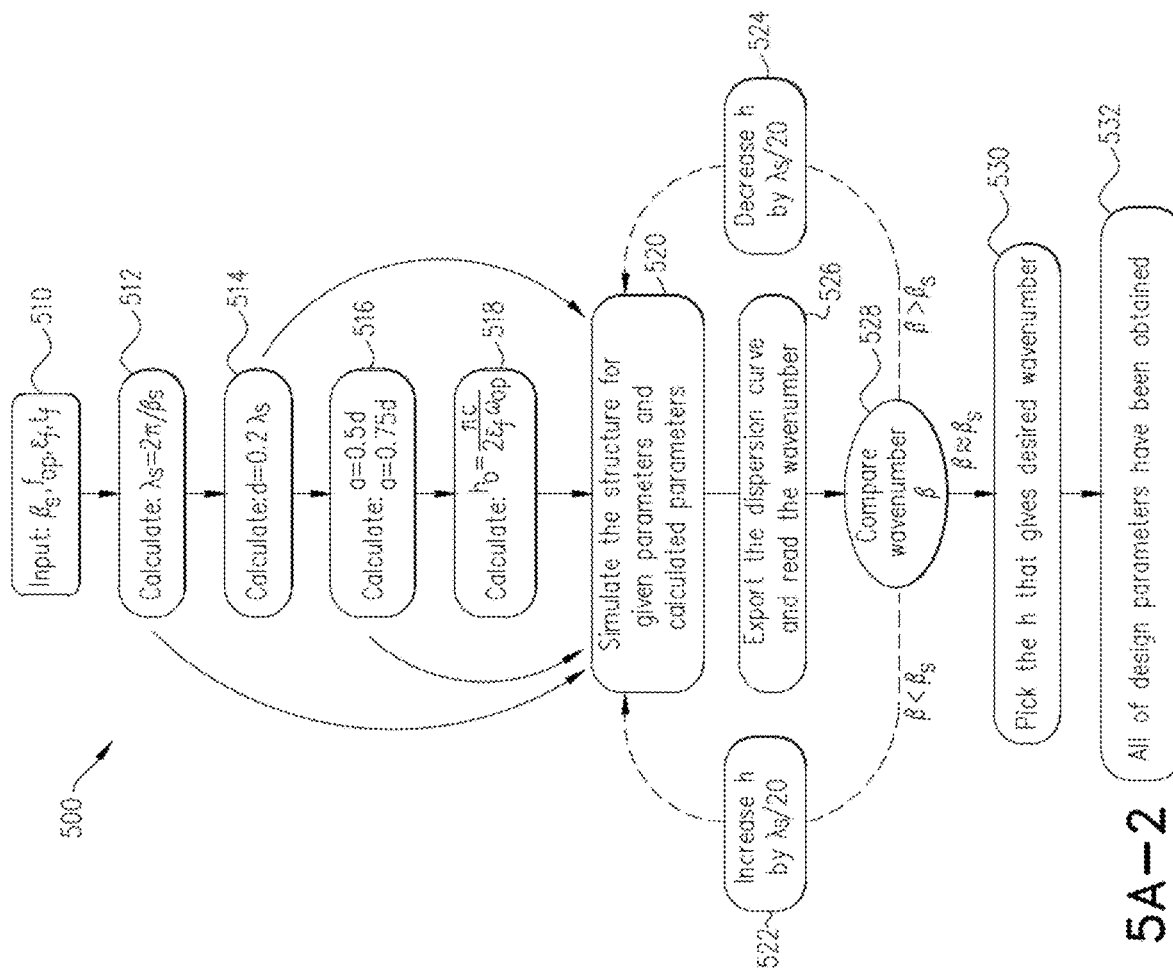
FIG. 5A(1) is a schematic illustration of the metamaterial textile indicating various dimensions that may be controlled during the metamaterial textile design, according to embodiments of the present disclosure.
Figures 1, 5A:
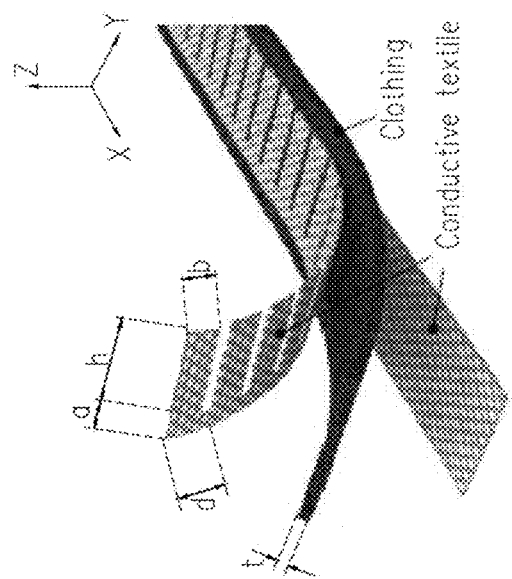

Reference is now made to FIG. 1A, which is a schematic illustration of a sensor network interconnected by radio-waves confined on clothing. Devices in the network may exchange energy and information through the evanescent field of surface waves rather than radiation into the surrounding space. According to FIG. 1A, networks based on metamaterial textiles may be interconnected by radio-wave surface plasmons that propagate along structures patterned on clothing worn by a user. In some embodiments, the network may comprise a smart-clothing hub to enable connection of multiple devices or sensors along the network illustrated in FIG. 1A.

Reference is now made to FIG. 1B, which is a schematic illustration of a structure of the metamaterial textile, according to embodiments of the present disclosure. According to some embodiments, the metamaterial textile is comprised of a sheet of metamaterial textile cut into a comb shape. The comb shaped metamaterial textile 110 may comprise a long base 120 with a plurality of teeth 122 extending along and from the base 120, wherein a gap, e.g., gap 124, is present between every two adjacent teeth 122.

According to some embodiments, the comb shaped metamaterial textile 110 may comprise a non-conductive layer 112, e.g., clothing, attached to the comb shaped metamaterial textile 110. The non-conductive layer 112 typically being located beneath the comb shaped metamaterial textile 110.

According to some embodiments, the comb shaped metamaterial textile 110 may further comprise a protective conductive layer 114 attached to and located beneath the non-conductive layer 112.

The configuration of the metamaterial textile of the present disclosure, comprising at least three layers of metamaterial shaped as a comb with teeth and gaps therebetween, at certain dimensions and distances from one another, and the addition of a non-conductive layer as well as a protective layer, may ensure that the signals do not enter the body of the clothing wearer nor radiate in space, but that the signals are rather designed to propagate along the comb shaped metamaterial textile with little to no signal loss.

According to some embodiments, a minimum number of teeth to enable propagation of radio-surface plasmons along the comb shaped metamaterial textile may be two, i.e., at least two teeth or two units are required in order to provide sufficient wireless transmission, while a maximum number of teeth to enable propagation of radio-surface plasmons along the comb shaped metamaterial may be limited by the total length and conductivity of the metamaterial textile, which may be approximately 100 teeth or units.

Reference is now made to FIG. 1C, which is a schematic illustration of simulation of the electric field distribution |Ez| emitted by a dipole above a metamaterial textile (top figure), unpatterned conductive textile (middle figure), and nonconductive textile (bottom figure), the textile is placed on the body modeled by air-tissue half-space, according to embodiments of the present disclosure. Numerical simulations demonstrate the ability of the metamaterial textile to confine electromagnetic radiation from a dipole transmitter at short-range communication frequencies (2.4-2.5 GHz industrial, scientific, and medical (ISM) band, including Bluetooth and Wi-Fi protocols). FIG. 1C illustrates that placement of a transmitter 5 mm above the structure excites surface plasmons that propagate to the receiver with high efficiency and minimal radiation into the surrounding space.

Reference is now made to FIG. 1D, which is a schematic illustration of normalized field distribution on the 'yz' plane and field profile along the dashed line, according to embodiments of the present disclosure. The 'back' denotes the back side of the wearer of the metamaterial textile, while 'front' denotes the front side of the wearer of the metamaterial textile. It is clear that the field distribution and signal strength is much higher as closer the signal is to the metamaterial textile, located at the front side of the wearer.

These surface modes are absent in conductive textiles that are not structured, in which case transmission occurs in the radiative mode with about four orders-of-magnitude lower efficiency. The textiles may be folded with minimal radiative losses and reflection (<5†% for U-turn with 1.25-mm radius-of-curvature).

Reference is now made to FIG. 1E, which is a schematic illustration of a dispersion curve of the metamaterial structure, according to embodiments of the present disclosure. The shaded gray area shows the 2.4-2.5 GHz ISM band.

FIG. 1F is a schematic illustration of comparison of the normalized power flow (peak value of the Poynting vector) with distance from transmitter near the textile (confined) and in free-space (radiative), according to embodiments of the present disclosure.

The surface plasmon-like nature of the modes are confirmed by the exponential field decay (FIG. 1E) and asymptotic dispersion curve (FIG. 1F), whose characteristics may be controlled by simply tuning the geometry of the structure (FIG. 1B). Propagation losses are dictated by the textile conductivity and are estimated to be less than 0.2 dB/cm for moderate conductivities $>2\times10^5$ S/m. Notably, signals emitted by standard wireless devices are confined on the metamaterial textile without modification of the antenna, although optimized designs could further enhance the preferential excitation of surface waves over radiative modes.

Reference is now made to FIGS. 2A-2C, which are schematic illustrations of devices constructed from the metamaterial textiles: (A) power divider. (B) antenna, and (C) ring-resonator, respectively, according to embodiments of the present disclosure. Metamaterial textiles provide a versatile platform for building radio-wave circuits that manipulate wave propagation around the body. Three basic building blocks for such circuits may be: a power divider (FIG. 1A), antenna (FIG. 1B), and ring resonator (FIG. 1C). The devices may be fabricated by laser-cutting conductive textile (Cu/Ni polyester) and attaching the patterns to a cotton-polyester athletic shirt, or any other piece of clothing. The power divider device (FIG. 2A) may evenly split an input signal between the two output ports, enabling the distribution and combination of signals from multiple devices.

Reference is now made to FIGS. 2D-F, which are schematic illustrations of Simulation (left) and near-field measurement (right) of the normal component of the electric field above the textile surface during continuous wave excitation at position 1 with a dipole probe. Scale bar is 5 cm, and further to FIGS. 2G-I, which are schematic illustrations of transmission spectra between antennas placed 5 mm above labeled positions on the body, according to embodiments of the present disclosure. White arrow in (B) indicates that the probe is placed 10 cm above the textile to measure the radiative field.

Device functionality is validated by the close agreement between numerical simulations and near-field measurements (FIG. 2D) as well as port measurements on the body (FIG. 2G). The antenna device (in FIG. 2B) may launch an input signal from confined wave as radiation into the surrounding space for short-range transmission, such as from the shoulder of a user to an ear-worn device.

Simulations and field mapping show excitation of a resonant antenna mode (FIG. 2E), and measurements from a receiver placed approximately 10 cm above the antenna indicate radiation within the 2.4-2.5 GHz band (FIG. 2H). Finally, the ring resonator (in FIG. 2C) may exhibit a series of resonances that may be used to filter signals, sense mechanical strain, and enhance interactions with nearby objects. Simulations and field mapping reveal a whispering gallery mode of order m=7 at 2.5 GHz (FIG. 2F), which corresponds to a sharp resonant dip in the transmission spectrum between two diametrically opposite points (FIG. 2I). Close agreement between measurements on and off the body suggest robustness to environmental effects. Circuits built from these basic devices may perform sophisticated functions for applications in energy transfer, sensing, and signal processing.

Reference is now made to FIG. 3A, which is a schematic illustration of wireless network of two Bluetooth nodes (sensors 1 and 2) simultaneously transmitting data to a smartphone (hub). FIG. 3A illustrates the ability of the metamaterial textile to enhance the transmission of wireless signals between devices worn on the body. FIG. 3A illustrates a network of two sensor nodes, consisting of commercial Bluetooth modules attached to the left shoulder and lower back of a user, and a central hub (smartphone) worn on the abdomen of the user. Full-wave simulations of the sensors transmitting in a computational body model show confinement of energy onto the textile surface and propagation around the curvature of the body of the user.

Reference is now made to FIG. 3B, which is a schematic illustration of full-wave simulations of wireless transmission in a computational human body model. Dashed lines show the cutting planes and white dots the transmitting sensor. In contrast to FIG. 3A, radiative communication performed in absence of the metamaterial textile results in about three orders of magnitude lower efficiency due to radiative losses and obstruction by the body of the user.

Figure 3F:
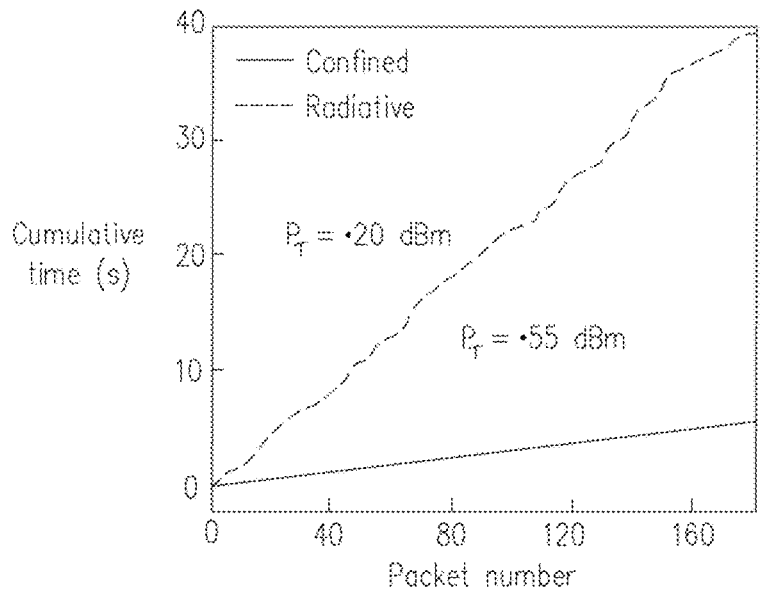
FIG. 3F is a schematic illustration of cumulative transmission time as a function of number of packets, according to embodiments of the present disclosure.

Reference is now made to FIG. 3C, which is a schematic illustration of a relative signal strength indicator (RSSI) recorded by the smartphone from each sensor during physiological activity, according to embodiments of the present disclosure. Reference is further made to FIG. 3D, which is a schematic illustration of a comparison of RSSI averaged across each activity, while Error bars show s.d. (n=3 subjects), to FIG. 3E, which is a schematic illustration of wireless transmission (Bluetooth) latency as a function of transmit power, while error bars show s.d. (n=60 packets), and to FIG. 3F is a schematic illustration of cumulative transmission time as a function of number of packets, according to embodiments of the present disclosure.

To experimentally test the robustness of this effect, real-time monitoring of the signal strength was performed with the smartphone on subjects during physiological activity. Controls were conducted by repeating the activity protocol without the metamaterial textile. FIG. 3C illustrates that the relative signal strength indicator (RSSI) from one subject during 5-min durations of standing, walking, and running was enhanced by about 31~dB for both devices. Across a group of subjects (n=3), the enhancement averaged over each activity was ~32.1 dB for the shoulder device and 32.7 dB for the back device (FIGS. 3C-3D). These three orders of magnitude enhancement of signal transmission efficiency translate into lower power consumption and higher communication throughput. In particular, enhanced signal transmission enabled operation of the sensor at the lowest available transmit power setting (−55 dBm) without significant increase packet latency (FIG. 3E). In contrast, connection could not be established at power levels below −24~dBm in absence of the textile. Cumulative measurements show a rate of 4.53 packets per second for the radiative system and 31.86 packets per second for the metamaterial textile system at the lowest power setting where connection may be established (FIG. 3F). This enhancement translates directly to longer sensor battery lifetimes since wireless communication is typically among most energy demanding of sensor functions.

Figure 3G:
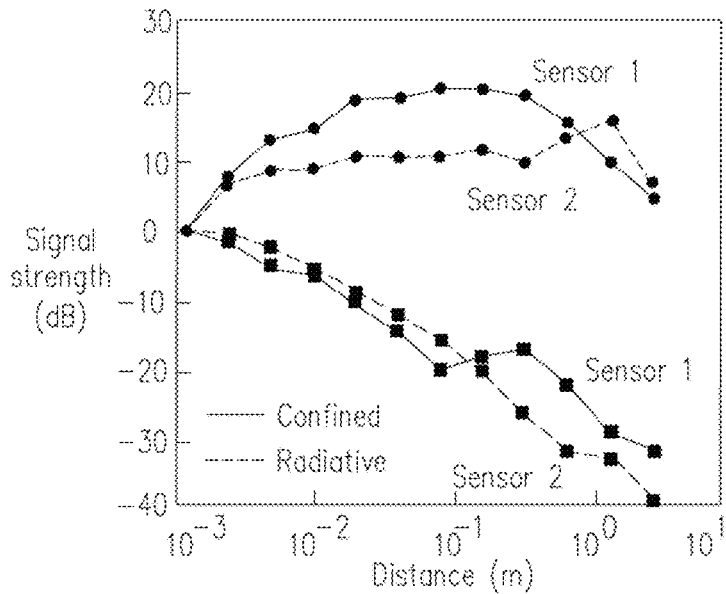
FIG. 3G is a schematic illustration of signal strength from sensors as a function of distance from the position of the smartphone, according to embodiments of the present disclosure.

Reference is now made to FIG. 3G, which is a schematic illustration of signal strength from sensors as a function of distance from the position of the smartphone, according to embodiments of the present disclosure. Data security is essential for the transmission of health and other personal data on body networks. FIG. 3G illustrates the change in signal strength from the sensors as a function of distance from the abdomen of the user. The signal strength profile for the radiative system exhibits an increase in strength at distances less than 20~cm for the shoulder and 1~m for the back sensors due to the obstruction of propagation by the body, followed by radiative decay with distance. In contrast, the network based on radio-wave confinement is characterized by an exponential decay away from the body, resulting in about 40 dB lower signal strength at a distance of 2.5 m from the body. This localization of energy near the body provides security at the physical layer of communication that is complementary to approaches based on encryption or protocol. In addition, radio-wave confinement may suppress interference between neighboring networks and eliminate the need for spectrum sharing protocols. Such personal networks immune to interference could enable individual utilization of full radio bands without degradation of performance from nearby devices.

Figure 4B:
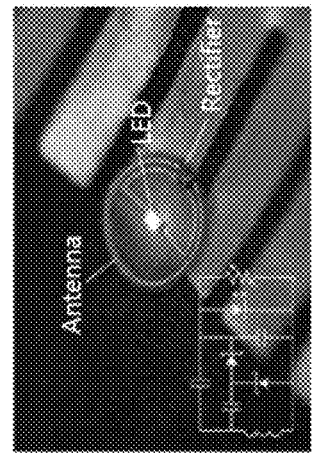
FIG. 4B is a schematic illustration of an image of the energy harvesting unit on the metamaterial textile and its circuit schematic, according to embodiments of the present disclosure.
Figure 4C:
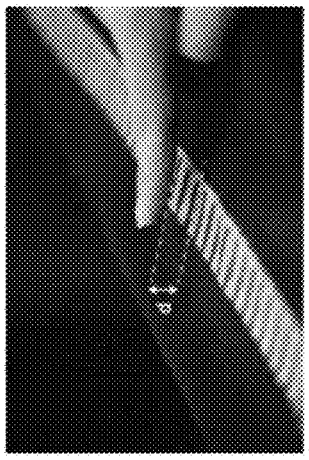
FIG. 4C is a schematic illustration of contactless sensing of finger proximity at distance d from the metamaterial textile, according to embodiments of the present disclosure.
Figure 4E:
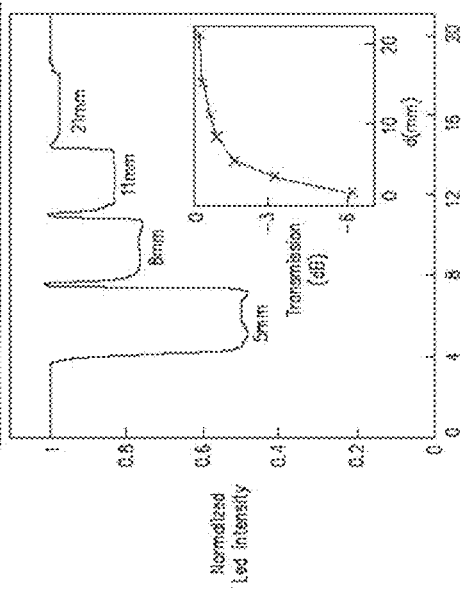
FIG. 4E is a schematic illustration of sensing of finger proximity from the metamaterial textile, according to embodiments of the present disclosure.
Figure 4A:
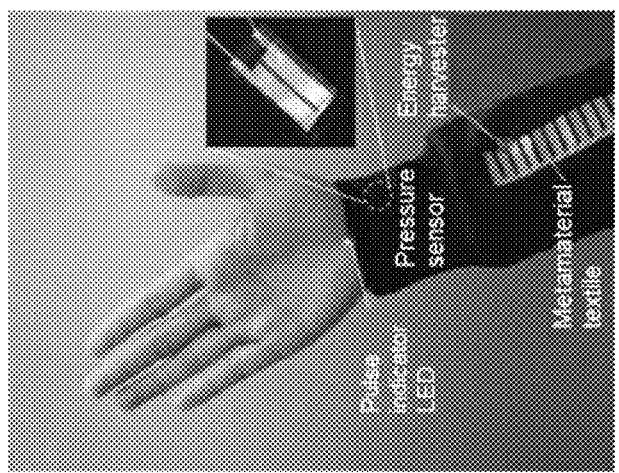
FIG. 4A is a schematic illustration of an image of a wrist-worn pulse sensor wirelessly powered by radio-waves guided along a metamaterial textile sleeve, according to embodiments of the present disclosure.

Reference is now made to FIG. 4A, which is a schematic illustration of an image of a wrist-worn pulse sensor wirelessly powered by radio-waves guided along a metamaterial textile sleeve. The pulse sensor comprises of an energy harvesting unit, pressure sensor, and LED for visual indication. The pressure sensor is placed under the textile on the wrist. The confinement of radio-waves on metamaterial textiles also enables wireless power transfer to many classes of low-power sensors. As a demonstrative example, a pulse indicator was wirelessly powered on the wrist of a user by guiding energy along a long-sleeved sweater along the length of the user's arm.

Reference is now made to FIG. 4B, which is a schematic illustration of an image of the energy harvesting unit on the metamaterial textile and its circuit schematic. The pressure sensor (not shown) is represented by the variable resistor in the circuit schematic. This sensor device provides a visual indication of the subjects heartbeat using a light-emitting diode (LED) coupled to a resistive pressure sensor and powered by an energy harvesting circuit.

Reference is now made to FIG. 4C, which is a schematic illustration of contactless sensing of finger proximity at distance d from the metamaterial textile, according to embodiments of the present disclosure. That is, according to FIG. 4C, sensing may be performed even when no actual contact is made between the user and the sensor/metamaterial textile.

Figure 4D:
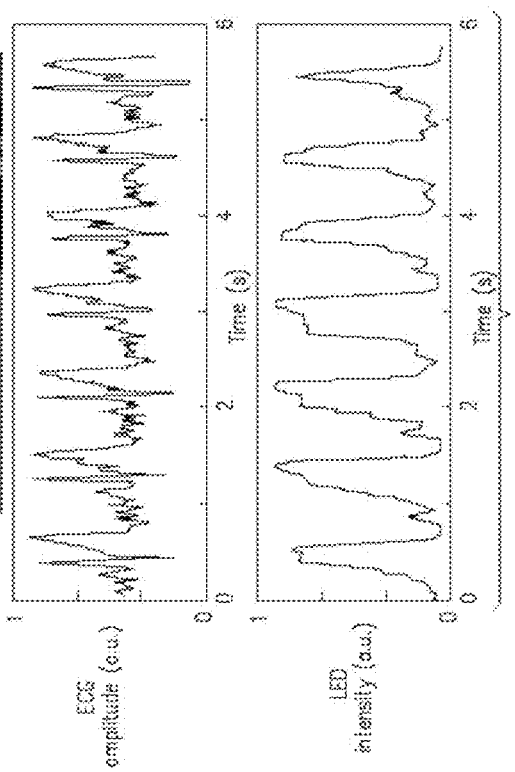
FIG. 4D is a schematic illustration of pulse detection and LED indication by the wireless sensor, according to embodiments of the present disclosure.

Reference is now made to FIG. 4D, which is a schematic illustration of pulse detection and LED indication by the wireless sensor. Recorded ECG is shown for comparison. According to FIG. 4D, the transmitter was placed on the shoulder of the user and the output power set to 20-dBm (100-mW, equivalent to a typical Wi-Fi transmitter). Monitoring the LED brightness during wireless power transfer revealed pulses that corresponded temporally with periodic cardiac activity recorded by electrocardiography (ECG). The transfer efficiency in this configuration was estimated to be 10.5% to the loop antenna and, including losses due to the rectifier, 3.5% to the LED. These power levels meet requirements for broad classes of low-power sensors, including temperature, pH, and other physiological markers, which consume less than 1-mW.

Reference is now made to FIG. 4E, which is a schematic illustration of sensing of finger proximity from the metamaterial textile. LED light intensity is modulated by the dependence of the transmission efficiency of the waveguide (inset) on finger distance. The interaction of surface waves with nearby objects also provides sensing capabilities in analogy to optical plasmonic sensors. As a proof-of-principle, FIG. 4E illustrates that placement of the index finger close to the metamaterial textile (less than 2 cm) during wireless powering of a LED resulted in a visually detectable decrease in LED brightness. This decrease can be attributed to the drop in transmission (FIG. 4E inset) that occurs when the field interacts with biological tissue, which exhibits high dielectric permittivity and absorption at radio frequencies. By tailoring the geometry of the metamaterial structure to change the localization of the surface plasmons, this sensitivity could be suppressed to improve robustness to environmental effects or further enhanced for applications in gesture sensing, proximity detection, and physiological monitoring.

Reference is now made to FIG. 5A(1), which is a schematic illustration of the metamaterial textile indicating various dimensions that may be controlled during the metamaterial textile design, according to embodiments of the present disclosure. According to some embodiments, 'a' denotes the width of the comb shaped base 120 (FIG. 1B), 'h' denotes the length of each comb shaped tooth 122, 'b' denotes the width of each tooth 122, and 'd' denotes the width of each tooth ('b') with the addition of the width of a gap 124, each gap 124 being located between two adjacent teeth 122.

Reference is now made to FIG. 5A(2), which is a schematic flow chart depicting a method for designing and accordingly manufacturing metamaterial textile, according to embodiments of the present disclosure. According to some embodiments, the conditions required for a metamaterial to support radio-frequency waves while bound to the surface of the body were examined.

The metamaterial textile may be designed by determining the geometrical parameters of the structure in order to support a surface mode with a desired wavenumber $\beta_s$ at the design frequency $f_0$. That is, in order to support a surface mode with a desired wavenumber $\beta$ s at frequency f0, the geometrical parameters of the metamaterial textile may be changed and controlled. The resulting surface plasmon wavelength is given by: $\lambda_s = 2\pi/\beta_s$. The decay length is: $\alpha_1^{-1} = 1/\sqrt{\beta_s^2 - (\omega/c)^2}$, where $\omega$ is the angular frequency and c is the speed of light. The decay length may determine the distance at which wireless devices may interact with the metamaterial textile. According to some embodiments, the decay length may be increased to enable greater range of communication with wireless devices or may be reduced for improved signal security.

According to some embodiments of the disclosure, the design procedure proceeds as follows:
(1) The length of each tooth or unit cell of the comb-like structure of the metamaterial textile is set to: $d = 0.2\lambda_s$. Simulations show that 'd' has negligible effect on $\beta_s$ if it is significantly subwavelength, while larger values of 'd' result in designs that are easier to fabricate.
(2) The parameters of the comb-like structure are set as a=0.5d and b=0.75d. These choices result in a comb structure that has large feature sizes and can be easily fabricated, but are otherwise arbitrary as simulations shows that $\beta_s$ is largely insensitive to 'a' and 'b' However, $\beta_s$ can be tuned over a broad range by 'h'.
(3) Parameter h is initialized to: $h_0 = \pi c/(4\pi\varepsilon_{tex}f_0)$, where $\varepsilon_{tex}$ is the relative dielectric permittivity of the textile.
(4) The width of the bottom non-conductive textile layer is set to: w=a+h. Larger choice of w results in greater suppression of signals coupling to the body, while smaller choice of w minimizes the area of conductive textile required.
(5) Given the thickness of the metamaterial textile, $t_f$, the dispersion curve of the structure is obtained by an eigenmode solver with varying 'h' between $0.5h_0$ and $2h_0$, yielding the value for which $\beta = \beta_s$.

Although in other embodiments, the initial values for 'd' 'a', 'b', and 'h' may be different, all of the abovementioned steps need to be performed in order to obtain a structure for which $\beta_s$ may be calculated.

A detailed explanation of the method according to some embodiments of the disclosure for designing and accordingly manufacturing metamaterial textile is hereby provided. A model of the interface between air and the body consisting of a half-space that is free-space in the upper region (z>0) and filled with biological material with a relative dielectric permittivity $\varepsilon_{body}$ in the lower region (z<0) was used. Taking x to be the direction of propagation, a thin planar metamaterial placed on the interface z=0 supports a mode whose electric field in the upper (E1) and lower (E2) region is given by $$E_n(r, t) = E_0 \begin{pmatrix} \frac{i\alpha_n}{\beta} \\ 0 \\ 1 \end{pmatrix} e^{i\beta x - \alpha_n|z| - i\omega t}$$

where $E_0$ is the field amplitude, $\omega$ the frequency, $\beta$ the wavenumber and $\alpha_n$ the decay parameter in each region. The form of equation (1) is dictated by symmetry considerations, while the design of the metamaterial determines the relationships between the parameters $\beta$, $\omega$ and $\alpha_n$. For a plasmonic metamaterial, $\beta$ and $\omega$ are related by a surface plasmon dispersion relation, whose curve lies to the right of the light line $\beta = \omega/c$, where c is the speed of light, and approaches an asymptotic limit termed the surface plasma frequency. The decay parameter for the free-space region is given by $$\alpha_1 = \sqrt{\beta^2 - \left(\frac{\omega}{c}\right)^2}$$

which, together with the dispersion relation, implies that the mode is bound to the upper surface because α1 is purely real. The lower region, however, supports additional bulk radiative modes within the region $\beta < \omega\sqrt{\varepsilon_{body}}/c$ due to the presence of biological tissue. Remarkably, these modes encompass nearly all frequencies below the surface plasma frequency because of the very high dielectric permittivity of biological tissue at radiofrequencies. To allow bound surface modes to exist on the body, the metamaterial should therefore support a single-sided mode $\alpha_2 \to \infty$ to prevent coupling to these bulk radiative modes and leakage into the lower region.

In addition to supporting surface modes, the metamaterial must also be able to interact with nearby sensors and devices without physical contact. The interaction of the surface waves with a wireless device can be described by expanding the electric field into forward (+) and backward (−) propagating surface modes $E(r,t) = (\alpha_+ e_+(r) + \alpha_- e_-(r))e^{-i\omega t}$, where $a_\pm$ are the mode amplitudes and $e_\pm(r) = p(y)[i\alpha_n/\beta, 0, 1]e^{\pm i\beta x - \alpha_n|z|}$ are the mode field patterns with a normalized profile function $$\frac{1}{2}\int |p(y)|^2 \, dy = \frac{\alpha_1 \alpha_2}{\alpha_1 + \alpha_2}.$$

When a radiofrequency source with current density j(r) is placed above the the modes are excited with amplitude $$a_\pm = -\frac{\beta}{2\omega\epsilon_0}\int j(r) \cdot e_\mp(r) \, d^3 r \quad (2)$$

Since e±(r) extends evanescently in the z direction, contactless excitation is efficient within a distance comparable to the decay length $\alpha_1^{-1}$ above the surface. In contrast, conventional waveguides, such as coaxial cables and microstrip lines, lack such an evanescent field and typically cannot be efficiently excited by nearby sources without specialized connectors.

The metamaterial can interact with a standard wireless device through the current density j(r) generated by its built-in antenna without any modification, although it should be noted that the excitation does not depend on conventional performance metrics such as directivity and gain. The orientation dependence of the interaction can be evaluated by approximating j(r) by its electric dipole moment p centred at $r_0$. Equation (2) then reduces $$a_\pm = \frac{i\beta}{2\epsilon_0}[p \cdot e_\mp(r_0)]$$

which shows that the dipole excites surface waves as long as it has a non-zero longitudinal (x) or vertical (z) component, because surface plasmon-like modes are transverse-magnetic.

Based on these physical considerations, the metamaterial must satisfy the following strict requirements to interconnect wireless networks with surface plasmon-like modes: (1) it must support a surface plasmon dispersion relation with cutoff frequency above the 2.4 2.5-GHz industrial, scientific and medical (ISM) band, (2) the field in the lower region must be screened such that $\alpha_2 \to \infty$ to minimize coupling with the body and (3) the wavenumber β of the surface modes must correspond to a decay length $\alpha_1^{-1}$ on the order of a few centimeters. These conditions are not met with existing metamaterials based on metal sheets or printed circuit boards. To develop a textile platform that meets these requirements, a metamaterial using a numerical optimization procedure for the planar structure in FIG. 1B is to be used.

This metamaterial structure consists of a planar comb-shaped pattern on the top layer (previously used as a plasmonic metamaterial), an intermediate fabric layer and a bottom layer comprising an un-patterned metallic conductor. The design procedure yields geometrical parameters such that the combined structure supports a surface plasmon dispersion that satisfies the requirements for wireless networking and has overall dimensions (2.5 cm width, 8 mm unit cell length) compatible with easy integration with most types of clothing by direct attachment of commercially available, low-cost conductive textiles.

The metamaterial shown in FIG. 5A(1) may support a surface plasmon dispersion of the form:

$$\beta = \frac{\omega}{c}\sqrt{\frac{\varepsilon_1 \varepsilon_2}{\varepsilon_1 + \varepsilon_2}} \quad \text{(i)}$$

where $\varepsilon_1$ is the permittivity of the dielectric and $\varepsilon_2$ is the permittivity of the metal.

Using the Drude model without damping, ε2 can be modelled as (ii)

$$\varepsilon_2 = 1 - \frac{\omega_p^2}{\omega^2}$$

where $\omega_p$ is a parameter analogous to the plasma frequency. The metamaterial has a negative permittivity parameter $\varepsilon_2 < 0$ at frequencies $\omega < \omega_p$. The resulting dispersion curve lies right of the light line and approaches a horizontal asymptote $\omega = \omega_{sp}$, where (iii) $\omega_{sp} = \omega_p/\sqrt{1+\varepsilon_1}$ is the surface plasma frequency. The parameters $\varepsilon_1$ and $\omega_p$ for the metamaterial textile may be found by fitting the numerically calculated dispersion curve to this model.

The metamaterial textile may be designed by determining the geometrical parameters of the structure to support a surface mode with a desired wavenumber $\beta_s$ at the design frequency $f_0 = 2.4$ GHz. By scaling the dimensions of the textile with the wavelength, the structure may be designed to support surface modes at frequencies between 10 MHz to 100 GHz. The resulting surface plasmon wavelength is given by $\lambda_{sp} \, 2\pi/\beta_s$ and the decay length (iv) $\alpha_1^{-1} =$ $$1/\sqrt{\beta_s^2 - \left(\frac{\omega}{c}\right)^2}$$

which determines the distance at which wireless devices may interact with the textile.

According to some embodiments, the method 500 for designing and accordingly manufacturing metamaterial textiles, may comprise the following operations.

In operation 510, the parameters $\beta_s$, $\beta_{0p}$, $\varepsilon_1$ and $t_1$ are determined.

In operation 512, $\lambda_s$ is calculated based on (v) $\lambda_{sp}=2\pi/\beta_s$, in operation 514, the length of the unit cell is set to $d=0.2\lambda_s$. Simulations show that d has negligible effect on $\beta_s$ (the design wavenumber of the frequency $f_0$) if it is significantly subwavelength (FIG. 5D), while larger values result in designs that are easier to fabricate. According to operation 516, the parameters of the comb-like structure of the metamaterial textile are set as a=0.5d and b=0.75d. FIGS. 5C-5D illustrate that $\beta_s$ is largely insensitive to a and b but can be tuned over a broad range by h.

According to operation 518, parameter h is initialized to (vi) $h_0=\pi c/(4\pi\varepsilon_{tex}f_0)$, where $\varepsilon_{tex}$ is the relative dielectric permittivity of the textile. In operation 518, the width of the bottom textile layer is set to (vii) w=a+h. This design suppresses nearly all coupling to the body (FIGS. 14A-14D) while minimizing the area of conductive textile required (FIGS. 15A-15B).

According to operations 520 the structure design is simulated for the given and calculated parameters.

In operation 526 the dispersion curve is exported and the wavenumber is read, given the thickness of the textile, tf, the dispersion curve of the structure is obtained by an eigenmode solver with varying h between $0.5h_0$ and $2h_0$, yielding the value for which, $\beta=\beta_s$, in operation 528.

The simulation may be repeated if $\beta<\beta_s$ or if $\beta>\beta_s$ through operation 522 in which h is increased by $\lambda_s/20$, or through operation 524 in which h is decreased by $\lambda_s/20$ respectfully.

In some embodiments, in operation 530, the h that gives the desired wavenumber is picked, and in operation 532, all the design parameters are obtained. According to embodiments of the present disclosure, the designed metamaterial textile supports the dispersion curve shown in FIG. 1E and fits the surface plasmon model with parameters $\varepsilon 1=4$ and $\omega_p=3.75\times 10^{10}$ rad m$^{-1}$.

According to some embodiments, numerical simulations have been implemented. For example, electromagnetic simulations were carried out with CST Microwave Studio (Dassault Systems). Field distributions were calculated using the finite-difference time-domain method using dipole excitation. Materials were assigned properties $\varepsilon_{tex}=1.5$ for textiles and $\varepsilon_{body}=40$ for tissue, while the computational body model used an anatomically accurate voxel model (Laura, CST Voxel Family) with resolution of 1.85×1.85× 1.25 mm. Dispersion curves were obtained by defining a unit cell of the structure and solving for the eigenfrequencies with periodic boundary conditions in the longitudinal directions and phase shift varying from 0 to $\pi$.

According to FIGS. 5B-5E, which are dispersion curves as the parameters a, b, d and h, respectively, are varied. Within the design range, the dispersion curve of equation (i) hereinabove is largely insensitive to the geometrical parameters except for h.

According to some embodiments, metamaterial textiles may be manufactured from conductive textile patterns, which were laser-cut (via Universal Laser Systems, VLS 2.30) from adhesive Cu/Ni polyester fabric sheets (Conductive Fabric Tape 86750, Laird Technologies: Conductive Non-woven Fabric 4770, Holland Shielding Systems). In some embodiments, patterns were attached on a cotton-polyester blend athletic shirt for radio-wave device and wireless communication experiments, and a cotton sweater for the wireless powering experiments.

According to some embodiments, the radio-frequency field above the textiles was measured using field mapping experiments to characterize the surface mode. The experiments used an electric field probe from the probe were measured by a spectrum analyser as the probe was scanned 5 mm above the textile surface with 2 mm step size. The surface modes were excited using a dipole with 1 cm length placed 2 mm above the input position, driven by a signal generator (Model 835, Berkeley Nucleonics).

According to some embodiments, transmission was measured as $|S_{21}|$ between two identical 1-inch short antennas (2.4 GHz, RN-SMA-S-RP, Microchip Technologies) connected to a vector network analyser (PicoVNA 106, Pico Technology) using coaxial cables (SMA-SMA, 50Ω, Amphenol). The spacing between the antennas and the textile surface was set to 2 mm using foam separators.

According to some embodiments, wireless communication was performed using the Bluetooth low energy (BLE) protocol. Sensor nodes made use of single-mode Bluetooth v4.0 modules (BL600, Laird Technologies) configured with an integrated antenna, a coin cell battery adapter (BA600. Laird Technologies) and a 3 V lithium battery (CR1632, Energizer). Sensors transmitted to a central hub consisting of an Android smartphone running a connectivity application (nRF Connect, Nordic Semiconductor) that recorded the signal strength from each sensor. Latency measurements were performed using connectivity testing software (UwTerminalX, Laird Technologies) run from a laptop connected to a hub device (BL620, Laird Technologies) wirelessly connected to the sensor nodes.

According to some embodiments, wireless power transfer used a 1-inch short antenna (RN-SMA-S-RP, Microchip Technologies) placed on the textile surface for power transmission. The antenna was driven by a 2.4 GHz signal input directly from a signal generator (SMB100A, Rohde and Schwarz) at 20 dBm (100 mW). The wireless energy harvesting unit was implemented using flexible printed circuit boards (PCBs) integrating the loop antenna and interconnection traces, fabricated commercially (0.1-mm-thick polyimide, 0.5 oz Cu, Gold Phoenix Printed Circuit Board). The rectifier was assembled on a rigid PCB (R4-TG130 substrate, 1 oz Ag, Interhorizon Corporation Pte) by microsoldering (NAE-2A, JBC) the following components: (1) 10 pF capacitor (Johanson Technology, 250R05L100GV4T), (2) 10 nF capacitor (Murata Electronics, GRM0335C1HR20WA01D), (3) 0.2 pF capacitor (Murata Electronics, GRM0335C1ER50BA01D) and (4) Schottky diode (Skyworks, SMS7621-060). The PCBs were integrated together with a red LED chip (Lumex, SML-LX0603SRW-TR) by microsoldering. The pressure sensor was connected in parallel with the LED by copper wire to yield the wireless pulse sensor device.

According to some embodiments, evaluation of wireless sensor networks on the body was performed with six healthy subjects (three females and three males), aged 20 to 40 years. Subjects wore an athletic shirt integrated with metamaterial textiles with sensors attached on the back and shoulder, and a smartphone worn over the shirt above the abdomen using a waistband. The smartphone recorded the receive signal strength during indoor physiological activity (standing, walking and running) in 5 min trials with a 2 min rest period in between each trial. Controls were performed by repeating the activity protocol with an un-patterned athletic shirt. Evaluation of the wirelessly powered sensor was performed with one healthy volunteer. The subject was asked sit back and relax on a chair while a custom pulse sensor was attached to a wrist and electrodes on the arm (Red Dot Electrodes, 3M). The antenna was attached on a long-sleeved sweater integrated with metamaterial textiles at the shoulder and driven with a continuous-wave signal. For quantification, the light intensity from the pulse sensor was measured by using optical fibre connected to a Si amplifier detector (PDA26A-EC, Thorlabs). ECG measurements were simultaneously obtained from the electrodes using a custom amplifier. ECG and optical data were simultaneously recorded using a digital oscilloscope (PicoScope 6402D, Pico Technology).

According to some embodiments, the Pressure sensor was fabricated as follows: Microstructured pyramid films were fabricated from a 20:1 mixture of polydimethylsiloxane (PDMS) elastomer base and curing agent (Sylgard 184, Dow Corning). Polyethylene terephthalate (PET) film with 12 μm thickness was used as the substrate. The PDMS mixture was mixed for 1 min at 2,500 r.p.m. using a SpeedMixer (Flack-Tek) and transferred onto a silicon wafer mould pretreated with octadecyltrichlorosilane. The mixture was spin-coated on the mould at 1,000 r.p.m. for 30 s. A plasma-treated PET film substrate was placed on top of the degassed PDMS film and thermally cured for 4 h. The moulded PDMS film on the PET substrate was plasma-treated and coated with a thin layer of PEDOT:PSS (CLEVIOS PH1000; Heraues) that was premixed with 5 wt % DMSO and 0.1 wt % Zonyl FS-300. The conductive layer was dried in a 70° C. oven for 30 min before use. The pressure sensor was placed on top of the etched copper electrodes and sealed.

According to some embodiments, the Wirelessly powered, battery-free Bluetooth sensors were fabricated as follows: The sensor nodes were made from commercial BLE sensors (CYALKIT-E02) with an integrated power management component (S6AE103A) and temperature and humility sensors (Si7020-A20). The output terminals of the rectifier in the wireless energy harvesting unit were connected to the input of the power management component on the back side of the sensor. The sensors were attached onto the metamaterial textile with the antenna of the energy harvesting unit facing down and configured to transmit sensor data via BLE immediately when powered on. The data were wirelessly received using a smartphone and displayed using an application.

Figure 6A:
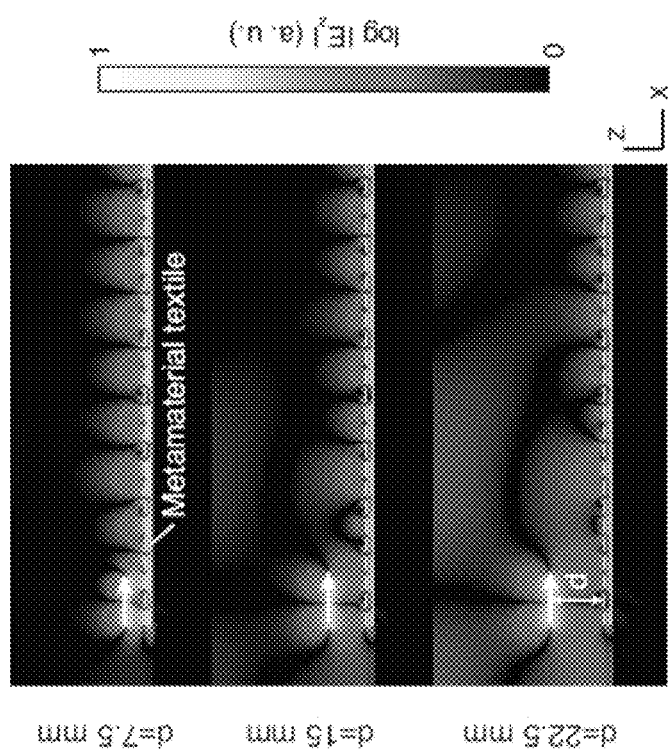
FIG. 6A is a schematic illustration of an electric field profile of the metamaterial textile with transmitter (horizontal electric dipole, 5 mm length) placed at varying distance d above the surface, according to embodiments of the present disclosure.
Figure 6B:
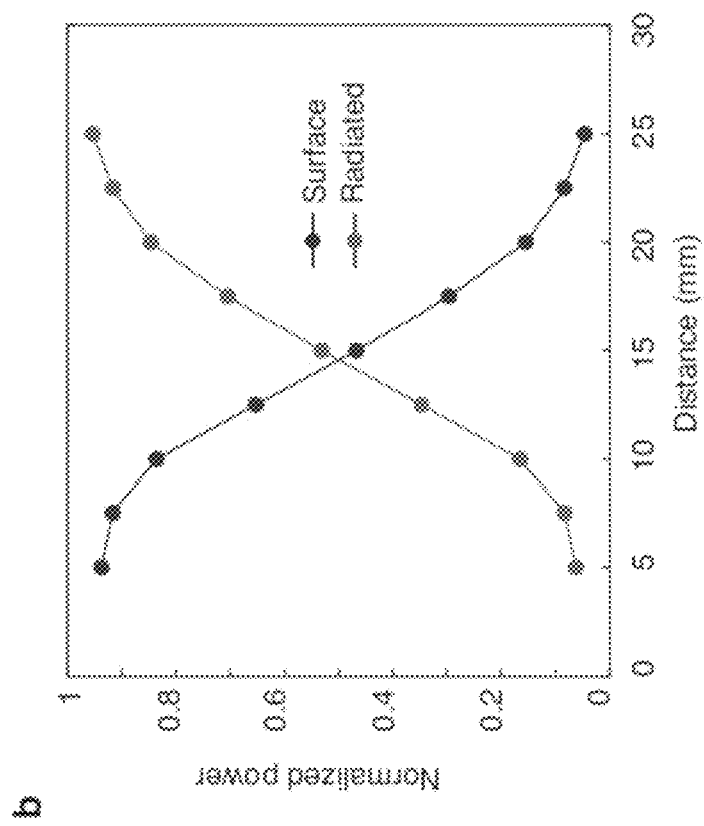
FIG. 6B is a schematic illustration of a fraction of power transmitted into the surface modes and radiative modes as a function of d, according to embodiments of the present disclosure.

Reference is now made to FIG. 6A, which is a schematic illustration of an electric field profile of the metamaterial textile with transmitter (horizontal electric dipole, 5 mm length) placed at varying distance d above the surface, according to embodiments of the present disclosure, and to FIG. 6B, which is a schematic illustration of a fraction of power transmitted into the surface modes and radiative modes as a function of 'd', according to embodiments of the present disclosure. The fraction of energy transmitted into surface modes versus radiative modes is controlled by the distance of dipole from the metamaterial textile, with preferential coupling to surface modes within 15 mm of the surface.

Figure 7A:
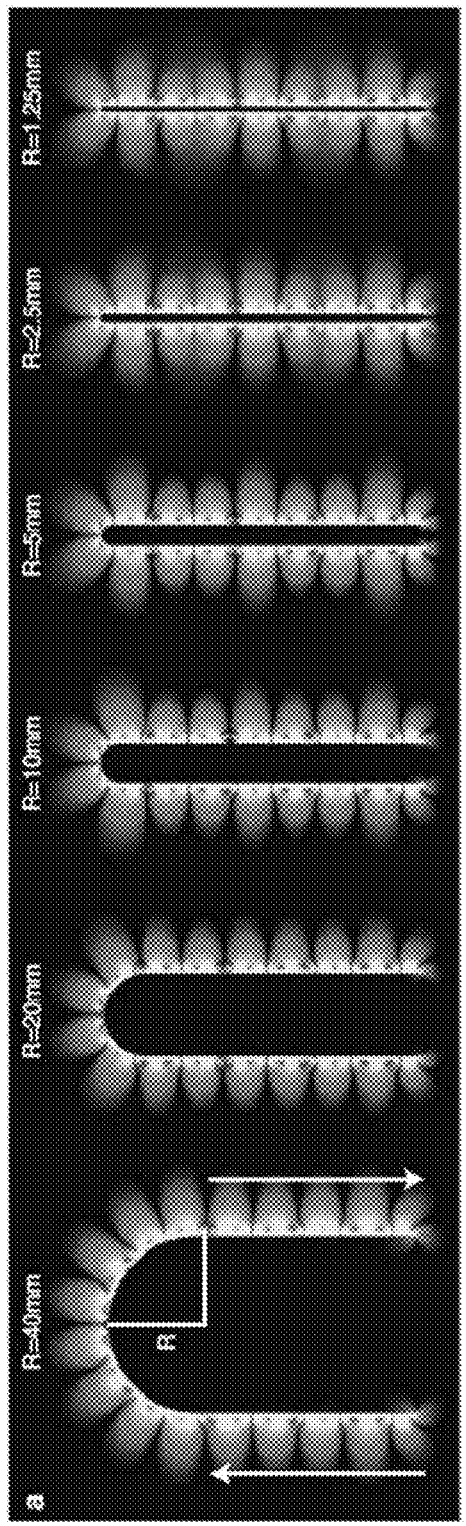
FIG. 7A is a schematic illustration of full-wave simulations of the electric field at 2.4 GHz for U-shapes with varying radii-of-curvature R, according to embodiments of the present disclosure.

According to FIG. 7A, which is a schematic illustration of full-wave simulations of the electric field at 2.4 GHz for U-shapes with varying radii-of-curvature R, the structure is excited at the bottom left point using a dipole placed 2 mm above the metamaterial textile. The propagation of surface waves is highly robust to folding and bending, and incurs minimal radiative losses and reflection with curvature (<5% for U-turn with 1.25-mm radius-of-curvature).

Figure 7C:
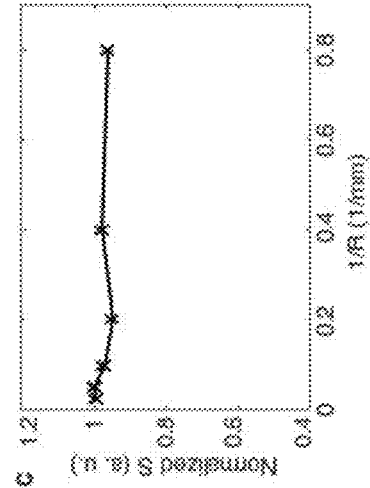
FIG. 7C is a schematic illustration of a normalized Poynting vector (peak value) as a function of 1=R at the bottom right point of the structure symmetric to the excitation point, according to embodiments of the present disclosure.
Figure 7B:
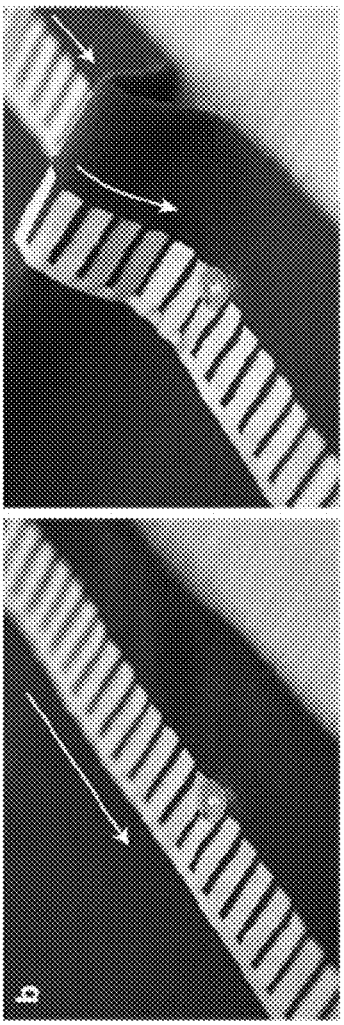
FIG. 7B is a Photograph of a wireless energy harvester (powering a red LED) placed on a flat and creased metamaterial textile, according to embodiments of the present disclosure.

Reference is now made to FIG. 7B, which is a photograph of a wireless energy harvester (powering a red LED) placed on a flat and creased metamaterial textile, according to embodiments of the present disclosure, and to FIG. 7C, which is a schematic illustration of a normalized Poynting vector (peak value) as a function of l=R at the bottom right point of the structure symmetric to the excitation point, according to embodiments of the present disclosure. The transmitter was placed directly above the textile and the output power set to 20 dBm.

Figures 8A, 8B, 8C:
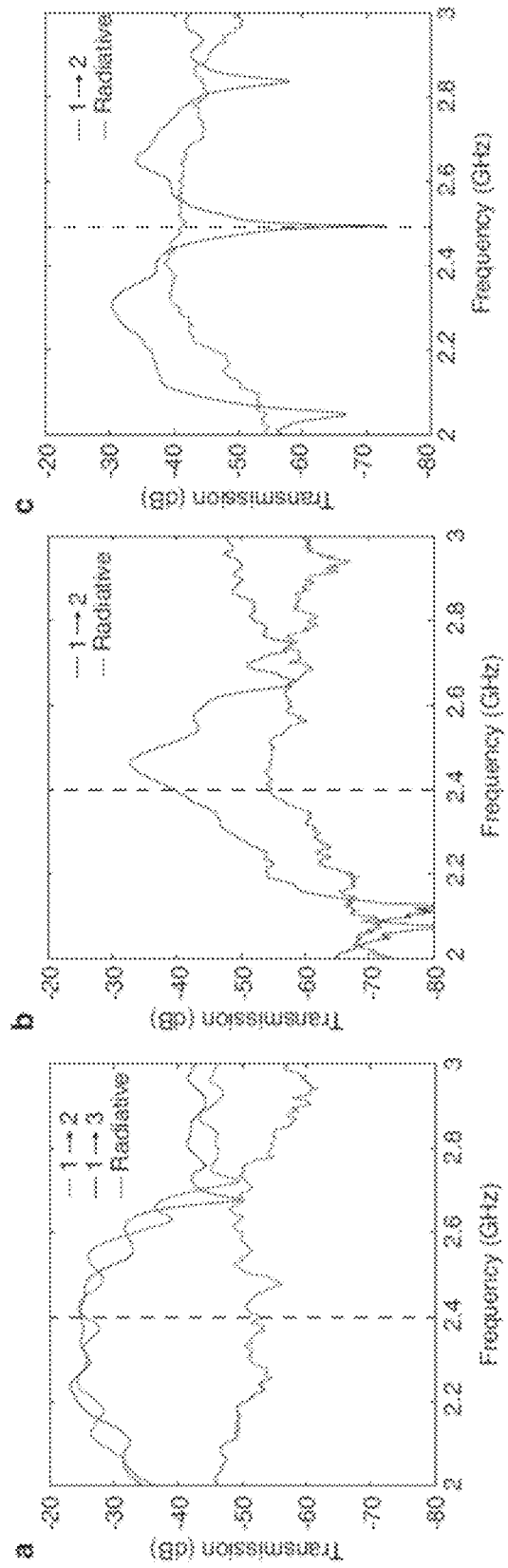
FIGS. 8A-8C are schematic illustrations of Transmission spectrum $|S_{nm}|$ for the power divider, antenna, and ring-resonator devices, respectively, measured in free-space without the human body, performed using two antennas placed above the port locations labeled in FIG. 6A, according to embodiments of the present disclosure.

FIGS. 8A-8C are schematic illustrations of transmission spectrum $|S_{mm}|$ for the power divider, antenna, and ring-resonator devices, respectively, measured in free-space without the human body, performed using two antennas placed above the port locations labeled in FIG. 6A, according to embodiments of the present disclosure. The power splitter evenly divides an input signal between the two output ports, enabling the distribution and combination of signals from multiple devices. A resonant antenna mode is measured using a receiver placed 10 cm above the antenna and indicates radiation within the 2.4-2.5 GHz band. The resonator comprised of a whispering gallery mode of order m=7 at 2.5 GHz (FIG. 2g), which corresponds to a sharp resonant dip in the transmission spectrum between probes placed at two diametrically opposite points, which may be used to sense textile stretching or used to perform signal filtering.

Figure 9A:
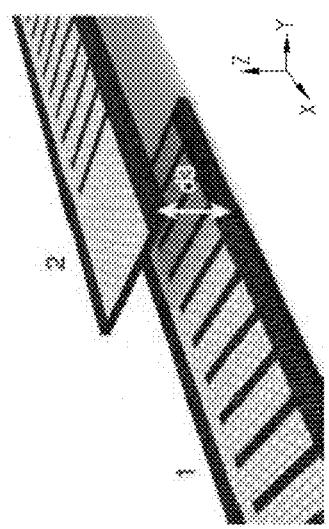
FIGS. 9A-9C are schematic illustrations of discontinuities in the conductive structure of the metamaterial textiles in the propagation direction x, transverse direction y, and vertical direction z, respectively, according to embodiments of the present disclosure.
Figure 9B:
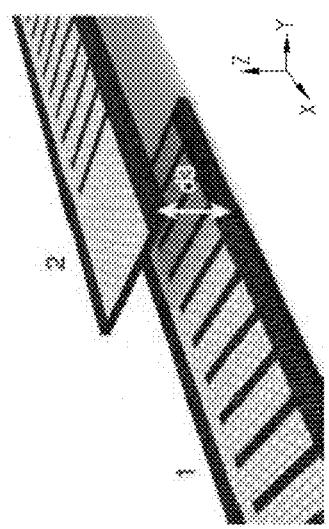
Figure 9C:
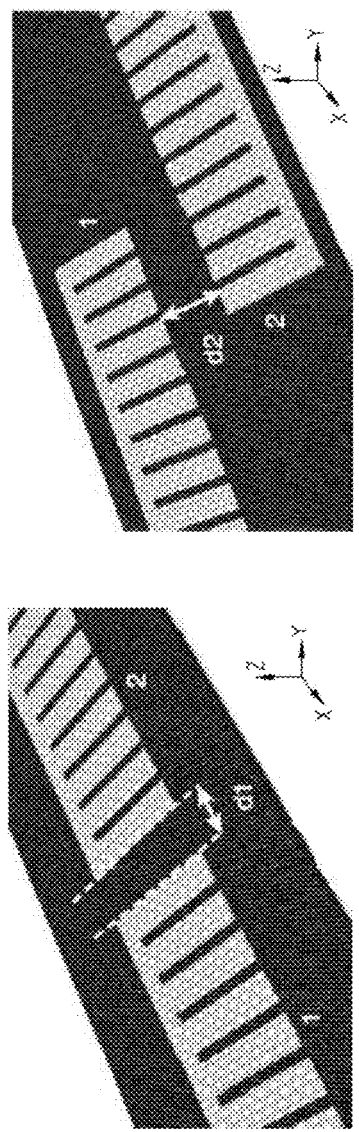
Figure 9D:
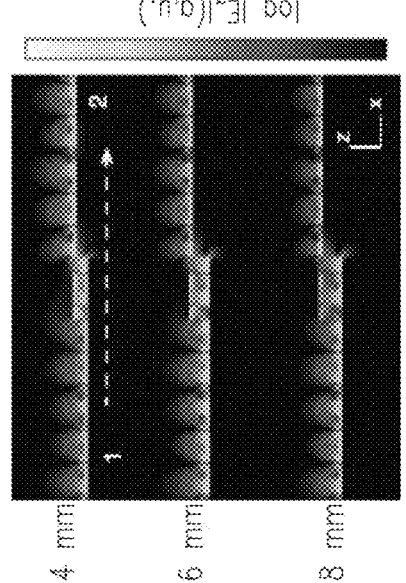
FIGS. 9D-9F are schematic illustrations of amplitude of the normal component of the electric field |Ez| for varying gap widths d1, d2, and d3, respectively, according to embodiments of the present disclosure.
Figure 9E:
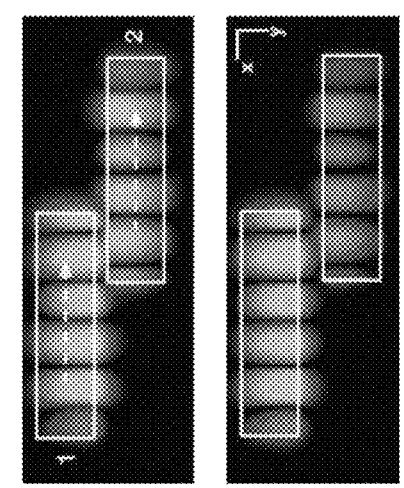
Figure 9F:
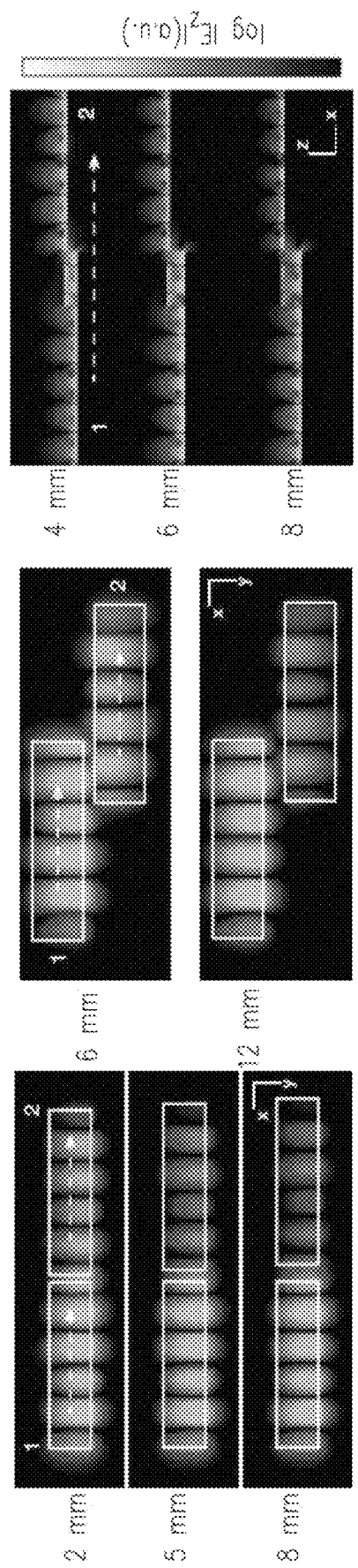
Figure 9G:
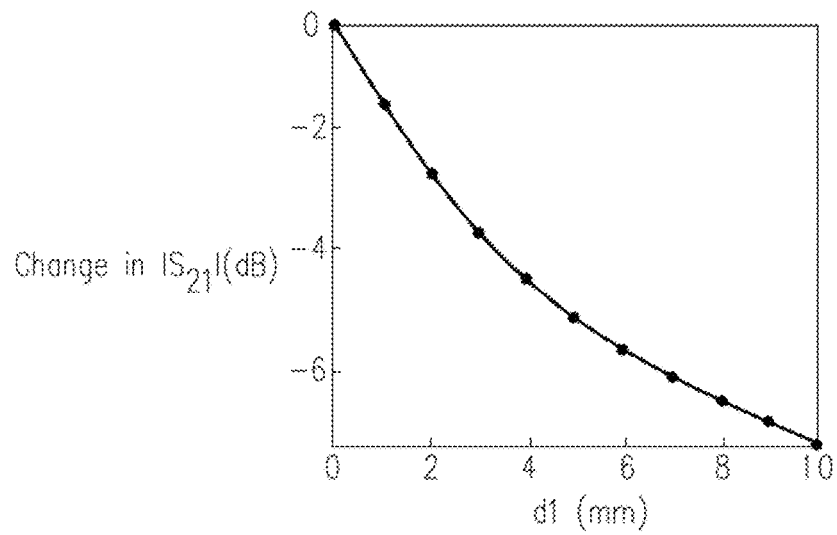
FIGS. 9G-9I are schematic illustrations of change in signal transmission $|S_{21}|$ as a function of gap width from d1=0, d2=6, and d3=2, respectively, according to embodiments of the present disclosure.
Figure 9H:
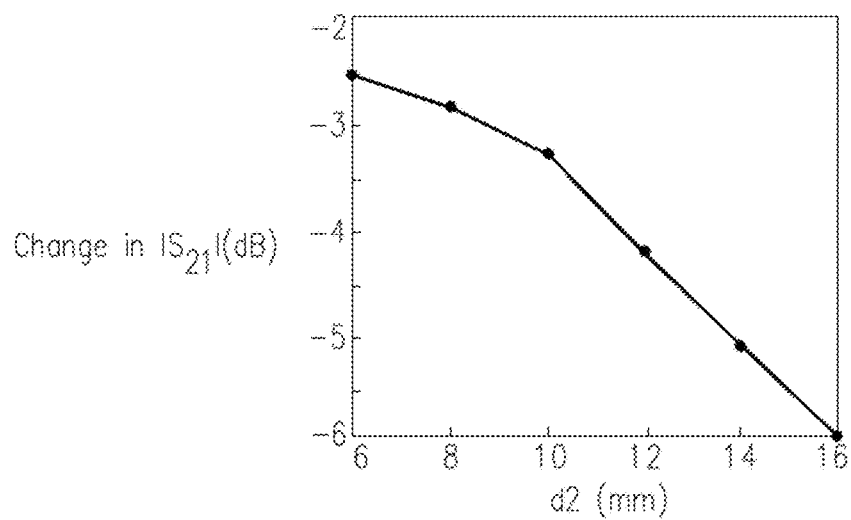
Figure 9I:
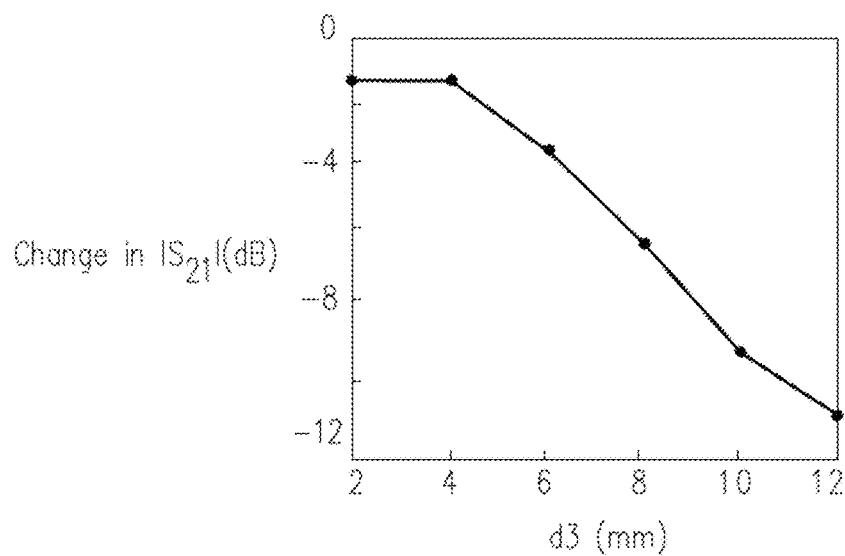

Reference is now made to FIGS. 9A-9C, which are schematic illustrations of discontinuities in the conductive structure of the metamaterial textiles in the propagation direction x, transverse direction y, and vertical direction z, respectively, according to embodiments of the present disclosure. FIGS. 9D-9F are schematic illustrations of amplitude of the normal component of the electric field |Ez| for varying gap widths d1, d2, and d3, respectively, according to embodiments of the present disclosure. The transmitter (receiver) is a horizontal dipole placed 5 mm above the surface at position labeled 1 (labeled 2). And FIGS. 9G-9I are schematic illustrations of change in signal transmission $|S_{21}|$ as a function of gap width from d1=0, d2=6, and d3=2, respectively, according to embodiments of the present disclosure.

Unlike conventional conductive textiles, signal propagation on metamaterial textiles is robust to discontinuities in the underlying conductive structure. Simulations illustrated in FIGS. 9A-9I show that the transmission efficiency across a 1 cm gap in the direction of propagation (x) is greater than −7 dB; the structures can also be discontinuous in the transverse (y) or vertical (z) directions with transmission efficiencies greater than −3 dB and −10 dB, respectively, for a 1 cm gap.

Figure 10A:
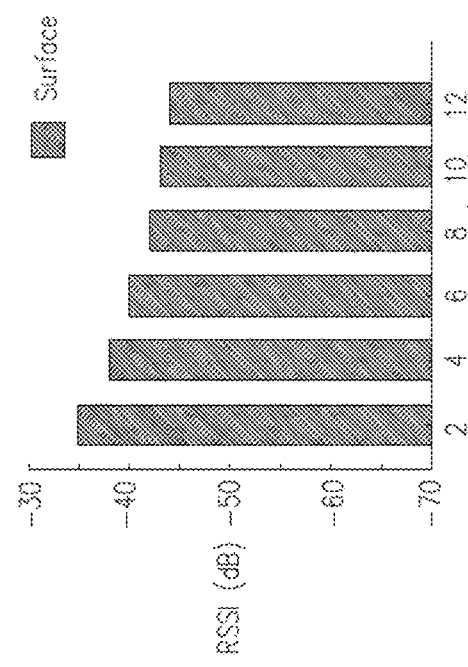
FIG. 10A is a schematic illustration of Bluetooth signal propagation across a gap between two textiles, according to embodiments of the present disclosure.
Figure 10B:
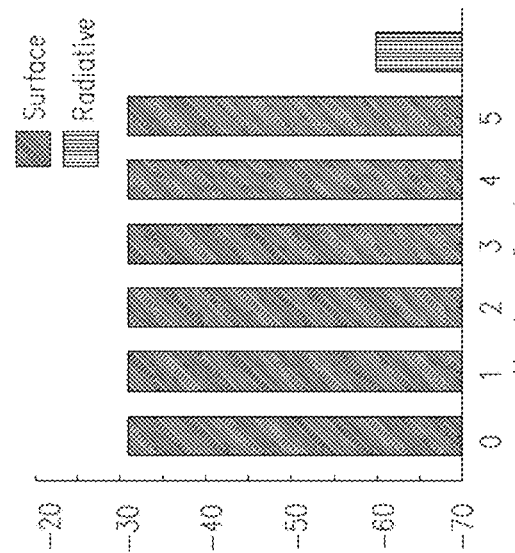
FIG. 10B is a schematic illustration of RSSI measured from a wireless receiver placed near the upper textile as the gap distance between the textiles is increased, according to embodiments of the present disclosure.
Figure 10C:
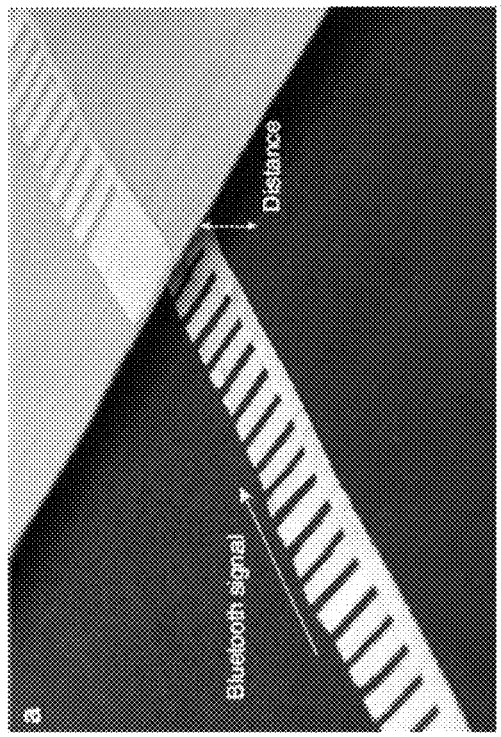
FIG. 10C is a schematic illustration of Bluetooth signal propagation on textiles cut with scissors, according to embodiments of the present disclosure.
Figure 10D:
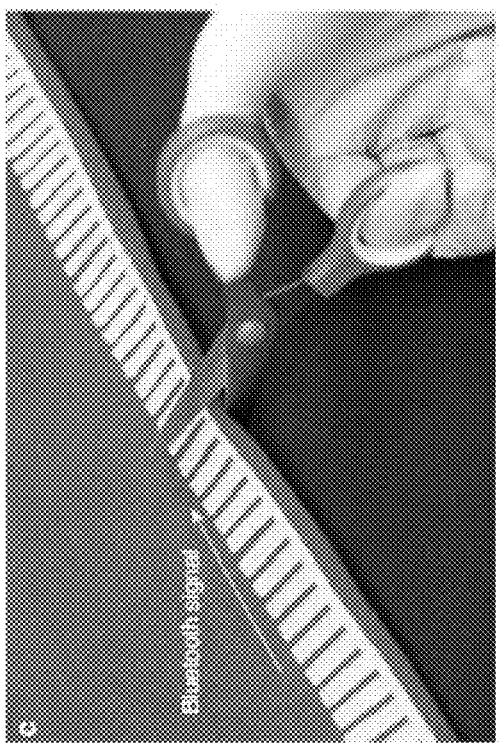
FIG. 10D is a schematic illustration of RSSI as a function of numbers of cuts, according to embodiments of the present disclosure.

FIG. 10A is a schematic illustration of Bluetooth signal propagation across a gap between two textiles, according to embodiments of the present disclosure. FIG. 10B is a schematic illustration of RSSI measured from a wireless receiver placed near the upper textile as the gap distance between the textiles is increased, according to embodiments of the present disclosure. FIG. 10C is a schematic illustration of Bluetooth signal propagation on textiles cut with scissors, according to embodiments of the present disclosure, and FIG. 10D, is a schematic illustration of RSSI as a function of numbers of cuts. Red bar shows RSSI measured in absence of the metamaterial textile.

Experimental measurements of wireless Bluetooth transmission along the metamaterial textile show a comparable transmission efficiency for a vertical gap as well as no detectable decrease in signal strength when the textile is cut at multiple locations (see FIGS. 10A, 10C). Such contactless transmission along the metamaterial textiles allows signals to efficiently couple between nearby structures and propagate from one article of clothing to another.

Reference is now made to FIGS. 11A-11B, which are schematic illustrations of instantaneous electric field amplitude and time-averaged power density S (logarithmic scale) for a dipole transmitter placed on the front (abdominal region) of a computational human body model without (radiative) and with (surface) the metamaterial textiles in FIG. 7A, according to embodiments of the present disclosure. The transmit power is the same in both configurations. The solid white lines show the power density contour line $S=S_{back}$ where $S_{back}$ is the power density at the location of receiver placed on the back of the body.

Reference is now made to FIG. 11C, which is a schematic illustration of power density radiated in front of the body along the dotted white line in FIG. 11A, according to embodiments of the present disclosure. Solid line shows $\infty 1/d^2$ fit, where d is the distance from the body. The distance in front of the body at which $S=S_{back}$ is estimated to be 22.4 m.

Data security is essential for the transmission of health and other personal data within body networks. Conventional wireless systems, however, are vulnerable to eavesdropping because signal transmission from sensor nodes on the body to another relies on radiation into the surrounding space. Due to obstruction by the body, the range at which a radiative signal can be intercepted is generally much larger than the separation distance between the devices. As an illustrative example, we performed full-wave simulations of radiative propagation from a transmit node on the abdomen to a receiver node on the back (FIG. 11B). The field intensity at the receiver is the same as at ~22 m in front of the subject (FIG. 11C); this eavesdropping range cannot be reduced by power control without compromising communication between the wearable devices. In contrast, metamaterial textiles localized the wireless signal within 10 cm of the body, enabling efficient transmission around the body without radiation into the surrounding space (FIG. 11B). This physical-layer security can complement cryptography and protocol-based approaches because it requires no additional computation or modification of the wireless device.

Figure 12A:
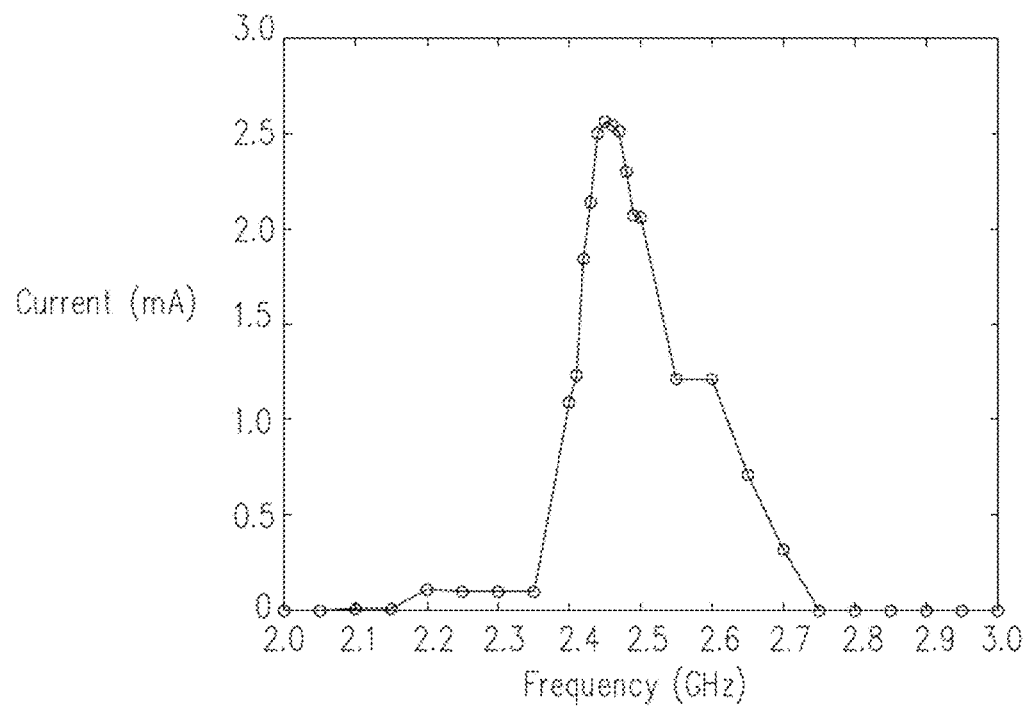
FIG. 12A is a schematic illustration of LED current as a function of frequency at an input power of 100 mW to an antenna placed above the metamaterial textiles, according to embodiments of the present disclosure.
Figure 12B:
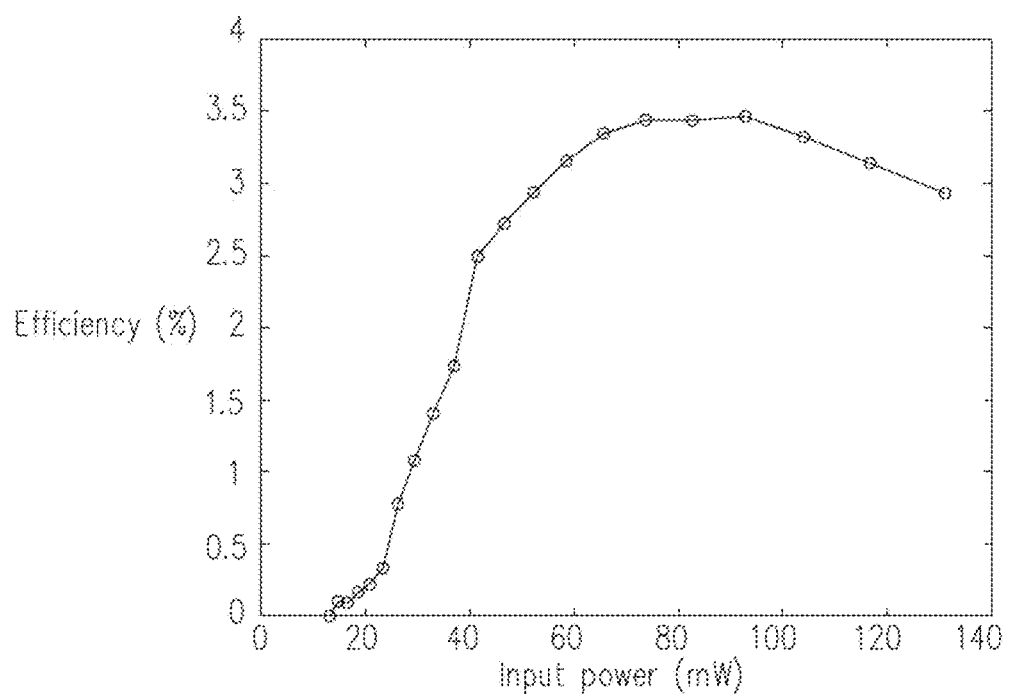
FIG. 12B is a schematic illustration of Wireless power transfer efficiency, measured as the power delivered to the LED (including nonlinear rectifier losses), as a function of input power, according to embodiments of the present disclosure.

Reference is now made to FIG. 12A, which is a schematic illustration of LED current as a function of frequency at an input power of 100 mW to an antenna placed above the metamaterial textiles, according to embodiments of the present disclosure, and to FIG. 12B, which is a schematic illustration of Wireless power transfer efficiency, measured as the power delivered to the LED (including nonlinear rectifier losses), as a function of input power, according to embodiments of the present disclosure. The efficient propagation of radio surface plasmons on metamaterial textiles enables wireless power transfer to many classes of low power sensor. As a demonstrative example, a pulse indicator was wirelessly powered on the wrist (FIG. 4A) by guiding energy along a long-sleeved sweater along the length of the arm. When powered, the pulse indicator provides a visual indication of the subject's heartbeat because the intensity of the light-emitting diode (LED) is modulated by a resistive pressure sensor that senses pulsation on the wrist of the user. The transmitter was placed on the shoulder and the output power set to 20 dBm (100 mW, equivalent to a WiFi transmitter). Monitoring the LED brightness during wireless power transfer shows that the pulses correspond to periodic cardiac activity recorded by ECG (FIG. 4D). The transfer efficiency in this configuration is estimated to be 10.5% to the loop antenna and, including losses due to the rectifier, 3.5% to the LED (FIGS. 12A-12B). These power levels meet requirements for many low-power sensors, including temperature, pH and other physiological markers, which consume less than 1 mW.

Figure 13C:
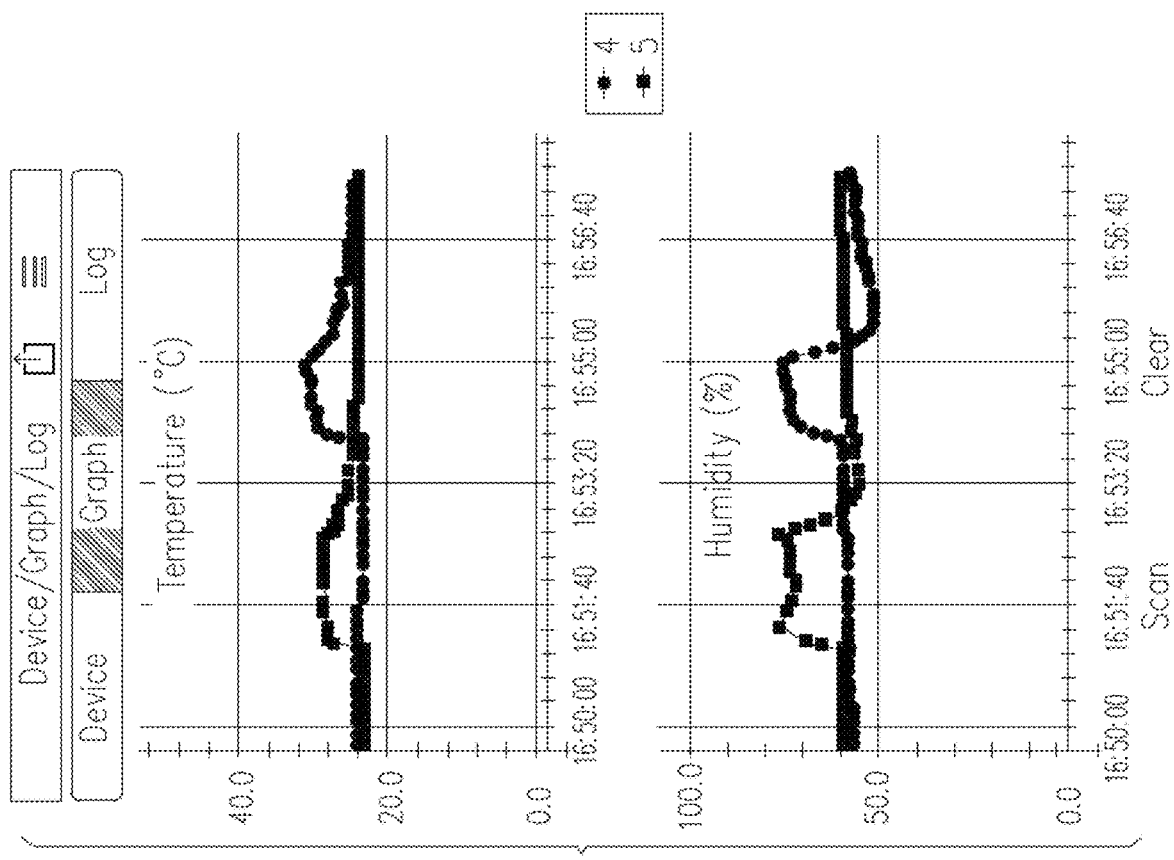
FIG. 13C is a schematic illustration of a screenshot of a smartphone application displaying data received from wireless sensor nodes on the shoulder and wrist (shown as nodes 4 and 5 respectively on the application) via propagation of Bluetooth signals along the metamaterial textile, according to embodiments of the present disclosure.
Figure 13A:
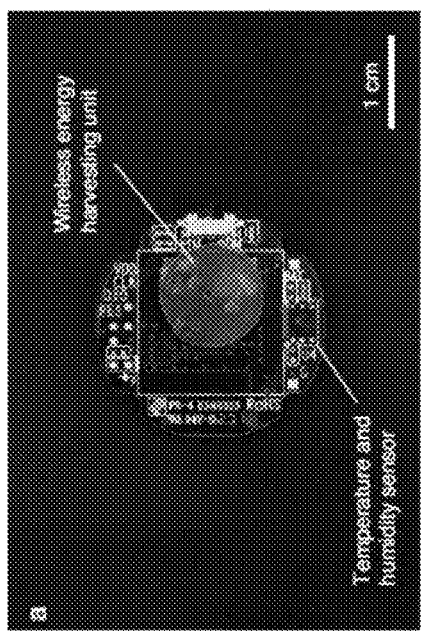
FIG. 13A is a schematic illustration of an image of the back of a sensor node integrated with a custom wireless energy harvesting unit, according to embodiments of the present disclosure.
Figure 13B:
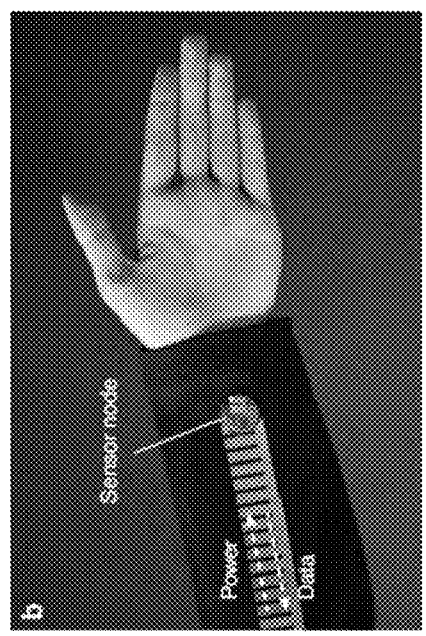
FIG. 13B is a schematic illustration of an image of the sensor node placed on the wrist of a user, while the second sensor node is placed on the shoulder of the user, according to embodiments of the present disclosure.

Reference is now made to FIG. 13A which is a schematic illustration of an image of the back of a sensor node integrated with a custom wireless energy harvesting unit, according to embodiments of the present disclosure. The output of the energy harvesting unit is directly connected to the power management circuit of the Bluetooth module. Reference is further made to FIG. 13B, which is a schematic illustration of an image of the sensor node placed on the wrist of a user, while the second sensor node is placed on the shoulder of the user, according to embodiments of the present disclosure, and to FIG. 13C, which is a schematic illustration of a screenshot of a smartphone application displaying data received from wireless sensor nodes on the shoulder and wrist (shown as nodes 4 and 5 respectively on the application) via propagation of Bluetooth signals along the metamaterial textile, according to embodiments of the present disclosure.

According to some embodiments, it was desired to demonstrate that wireless, battery-free sensors may be interconnected within the presently disclosed platform, accordingly, wirelessly powered Bluetooth sensor nodes may be placed on the shoulder and on the wrist of a user along the metamaterial textile. The sensor circuit is powered by a custom wireless energy harvesting unit and integrates a temperature sensor, a humidity sensor and a Bluetooth module that wirelessly transmits data to a smartphone placed near the body. Touching the sensors results in an increase in temperature and humidity, which may be detected by the respective sensors and displayed by an application on a smartphone. The distributed and synchronized capabilities of such wireless sensor networks could be used to monitor clinically important physiological signals such as pulse pressure propagation and electrical activity.

The interaction of surface waves with nearby objects also provides sensing capabilities in analogy to optical plasmonic sensors. The potential of metamaterial textiles of the present disclosure for human-machine interaction, an interactive smartphone application that changes the display image when an abrupt change in Bluetooth RSSI is detected, may be created. When the smartphone is placed near a metamaterial textile on which a Bluetooth signal is propagating, the display image can be changed by touching the textile with the index finger, even if the smartphone and the finger are not both in physical contact with the textile. Measurements show that the proximity of the textiles to biological tissue decreases the transmission by up to 6 dB, due to interaction with the surface wave. By tailoring the geometry of the metamaterial structure to modify the localization of the surface plasmons, this sensitivity to the proximity of biological tissue could be suppressed to improve robustness to environmental effects, or further enhanced for applications in gesture sensing, proximity detection and physiological monitoring. The conductive textiles according to the present disclosure may have conductivities between $2*10^5$ to $5*10^5$ S/m.

According to the present disclosure, the energy-efficient and secure interconnection of wireless sensor networks by confining radio-waves emitted by standard wireless devices onto metamaterial textiles, has been demonstrated. It is illustrated that the transmission efficiency of a wireless network may be enhanced by over three orders of magnitude compared to conventional radiative networks without metamaterial textile. Furthermore, it has been demonstrated that the wireless transmission of personal health data along a sleeve near the wrist is possible and that Bluetooth signals may be localized to within 10 cm of the body. Furthermore, it has been shown that the metamaterial textiles of the present disclosure may support the robust propagation of wireless signals, even across discontinuities in the conductive structure, and enable networks with new capabilities in wireless power transfer and wireless touch sensing. The results illustrated along the present disclosure highlight the potential of using clothing to engineer electromagnetic propagation around the body and provide a starting point for the translation of concepts from microwave and photonic circuits onto a textile platform for wireless sensing, signal processing and energy transfer. The metamaterial textiles of the present disclosure illustrate that endowing athletic wear, medical clothing and other apparel with such advanced electromagnetic capabilities may enhance the ability to perceive and interact with the world around us.

While this disclosure has been particularly shown and described with references to example embodiments thereof, it will be understood by those skilled in the art that various changes in form and details may be made therein without departing from the scope of the disclosure encompassed by the appended claims.

What is claimed is:

1. A metamaterial textile for providing wireless sensor network, said metamaterial textile comprising:
    a sheet of metamaterial textile cut into a comb shape comprising long base with a plurality of metamaterial textile teeth extending along and from the base, wherein a gap is present between every two adjacent teeth;
    wherein, the metamaterial textile is configured to enable propagation of radio-surface plasmons wave along the metamaterial textile for providing wireless sensor network, the radio-surface plasmons wave comprises a height;
    further wherein said metamaterial textile is configured to control the height of the radio-surface plasmons wave by changing number of the metamaterial textile teeth; and changing dimensions of the metamaterial textile teeth and changing dimensions of the gaps.

2. The metamaterial textile of claim 1, wherein the maximum number of teeth to enable propagation of radio-surface plasmons along the comb shaped metamaterial textile is 100.

3. The metamaterial textile of claim 1, wherein the minimum number of teeth to enable propagation of radio-surface plasmons along the comb shaped metamaterial textile is two.

4. The metamaterial textile of claim 1, wherein said comb shaped metamaterial textile is configured to be implemented as part of clothing.

5. The metamaterial textile of claim 1, wherein said comb shaped metamaterial textile comprises a non-conductive layer attached to the comb shaped metamaterial textile.

6. The metamaterial textile of claim 5, wherein said comb shaped metamaterial textile further comprises a protective conductive layer attached to and located beneath the non-conductive layer.

7. The metamaterial textile of claim 5, wherein said non-conductive layer attached to the comb shaped metamaterial textile blocks the propagation of radio-surface plasmons into body of a wearer of clothing.

8. The metamaterial textile of claim 5, wherein said non-conductive layer is textile.

9. The metamaterial textile of claim 1, wherein said comb shaped metamaterial textile is configured to form a ring-resonator.

10. The metamaterial textile of claim 1, wherein said comb shaped metamaterial textile is configured to form an antenna for transmitting data.

11. The metamaterial textile of claim 1, wherein said comb shaped metamaterial textile is configured to form a power divider for transmitting power to more than one location.

12. The metamaterial textile of claim 1, wherein said radio-surface plasmons wave has little to no signal loss even at low dB transmission.

13. A method for designing a metamaterial textile for providing a wireless sensor network, said method comprising:
    providing a metamaterial textile comprising: a sheet of metamaterial textile cut into a comb shape comprising a long base with a plurality of metamaterial textile teeth extending along and from the base, wherein a gap is present between every two adjacent teeth;
    providing wireless sensor network via propagation of radio-surface plasmons wave along the comb shaped metamaterial textile; and
    controlling height of the radio-surface plasmons wave by changing number of the metamaterial textile teeth, and by changing dimensions of the metamaterial textile teeth and dimensions of metamaterial textile gaps.

14. A method for designing a metamaterial textile for providing a wireless sensor network, said method comprising:
    providing a metamaterial textile comprising: a sheet of metamaterial textile cut into a comb shape comprising a long base with a plurality of metamaterial textile teeth extending along and from the base, wherein a gap is present between every two adjacent teeth, further wherein said comb shaped metamaterial textile comprises a non-conductive layer attached to the comb shaped metamaterial textile;
    setting value of width of each of the plurality of metamaterial textile teeth with the addition of width of a gap to: $d=0.2\lambda_s$;
    setting values of width of each of the plurality of metamaterial textile teeth and of width of the comb shaped base to specific values;
    setting value of length of each of the plurality of metamaterial textile teeth to:

$$h_0 = \frac{\pi c}{4\pi\varepsilon_{tex}f_0};$$

setting value of width of the bottom non-conductive layer to: $w=a+h$;
    providing thickness of the metamaterial comb shaped textile;
    implementing varying lengths of each of the plurality of metamaterial textile teeth between $0.5h_0$ and $2h_0$ into an eigenmode solver, thereby obtaining dispersion curve of the metamaterial textile;
    yielding the value for which $\beta=\beta_s$, wherein $\beta_s$ is desired wavenumber based on the dispersion curve; and
    calculating $\lambda_s=2\pi/\beta_s$, wherein $\lambda_s$ is surface plasmon wavelength for providing wireless sensor networks.

15. The method according to claim 14, wherein setting value of said width of each of the plurality of metamaterial textile teeth comprises setting the value to b=0.75d.

16. The method according to claim 14, wherein setting value of said width of the comb shaped base comprises setting the value to a=0.5d.

17. The method of claim 14, wherein setting value of width of each of the plurality of metamaterial textile teeth with the addition of width of a gap comprises setting the value according to a different equation than $d=0.2\lambda_s$.

* * * * *